(12) United States Patent
Dimitriou et al.

(10) Patent No.: US 7,927,271 B2
(45) Date of Patent: Apr. 19, 2011

(54) ENDOSCOPE TOOL COUPLING

(75) Inventors: John Dimitriou, Stow, MA (US);
Christopher A. Battles, Seymour, CT (US); Danial Ferreira, Milford, CT (US); Daniel Vigliotti, Hamden, CT (US); Patrick Gutelius, Monroe, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 1167 days.

(21) Appl. No.: 11/436,103

(22) Filed: May 17, 2006

(65) Prior Publication Data

US 2007/0270640 A1 Nov. 22, 2007

(51) Int. Cl.
*A61B 1/00* (2006.01)
(52) U.S. Cl. ......... 600/106; 600/104; 600/153; 600/154
(58) Field of Classification Search ............... 600/106, 600/174, 114, 117, 104, 102, 229, 121–125, 600/153–159; 277/177.1, 108
See application file for complete search history.

(56) References Cited

U.S. PATENT DOCUMENTS

| | | |
|---|---|---|
| 3,269,387 A | 8/1966 | Wallace |
| 4,240,411 A | 12/1980 | Hosono |
| 4,421,106 A | 12/1983 | Uehara |
| 4,474,174 A | 10/1984 | Petruzzi |
| 4,586,491 A | 5/1986 | Carpenter |
| 4,607,619 A | 8/1986 | Seike et al. |
| 4,676,230 A | 6/1987 | Miyazaki |

(Continued)

FOREIGN PATENT DOCUMENTS

EP 0 824 894 A1 2/1998
(Continued)

OTHER PUBLICATIONS

Machine Translation of JP Pub 09-103433A.*
(Continued)

*Primary Examiner* — Thomas J Sweet
*Assistant Examiner* — Ryan Henderson
(74) *Attorney, Agent, or Firm* — Wolf, Greenfield & Sacks, P.C.

(57) ABSTRACT

An endoscope tool coupling that facilitates the placement and positioning of a surgical tool within an endoscope. The tool coupling may be configured to accommodate differences in lengths between the surgical tool and the endoscope, which may allow a user to precisely position and maintain the distal end of a surgical tool in a desired location relative to the distal end of the endoscope despite differences and variations in lengths. The tool coupling may have an adjustable configuration to accommodate variations in tool and/or endoscope lengths. The tool coupling employ an arrangement that allows a user to easily increase or decrease the length of the coupling, such as by using a telescoping arrangement. A locking arrangement or mechanism may be provided to secure the coupling in a selected configuration for maintaining the surgical tool in a desired location relative to the endoscope. The tool coupling may be configured to generate a preload on the surgical tool when the tool is positioned in a desired location relative to the endoscope. The tool coupling may be configured to allow for the withdrawal and reintroduction of the same or a similar surgical tool without changing or impacting the original length adjustment and/or preload for the particular tool/endoscope arrangement. The tool coupling may be configured as a separate device that can be attached to various endoscopes, or the tool coupling may be an integrated component of the endoscope.

52 Claims, 13 Drawing Sheets

U.S. PATENT DOCUMENTS

| | | |
|---|---|---|
| 4,700,694 A | 10/1987 | Shishido |
| 4,705,023 A | 11/1987 | Arai |
| 4,710,171 A | 12/1987 | Rosenberg |
| 4,852,550 A | 8/1989 | Koller et al. |
| 4,920,953 A | 5/1990 | McGown |
| 4,957,486 A | 9/1990 | Davis |
| 4,967,732 A | 11/1990 | Inoue |
| 4,972,828 A | 11/1990 | Ito |
| 5,099,827 A | 3/1992 | Melzer et al. |
| 5,125,143 A | 6/1992 | Takahashi |
| 5,193,263 A | 3/1993 | Takahashi |
| 5,275,151 A | 1/1994 | Shockey et al. |
| 5,306,272 A | 4/1994 | Cohen et al. |
| 5,320,630 A | 6/1994 | Ahmed |
| 5,343,853 A | 9/1994 | Komi |
| 5,431,645 A | 7/1995 | Smith et al. |
| 5,456,673 A * | 10/1995 | Ziegler et al. .................. 604/264 |
| 5,460,167 A | 10/1995 | Yabe et al. |
| 5,556,367 A | 9/1996 | Yabe et al. |
| 5,556,371 A | 9/1996 | Schülken et al. |
| 5,575,754 A * | 11/1996 | Konomura .................... 600/117 |
| 5,631,973 A | 5/1997 | Green |
| 5,685,853 A | 11/1997 | Bonnet |
| 5,685,877 A | 11/1997 | Pagedas et al. |
| 5,695,491 A | 12/1997 | Silverstein |
| 5,696,837 A | 12/1997 | Green |
| 5,697,939 A | 12/1997 | Kubota et al. |
| 5,702,344 A | 12/1997 | Silverstein |
| 5,728,045 A | 3/1998 | Komi |
| 5,735,861 A | 4/1998 | Peifer et al. |
| 5,749,889 A | 5/1998 | Bacich et al. |
| 5,807,235 A | 9/1998 | Heff |
| 5,807,664 A | 9/1998 | Suzuki |
| 5,808,665 A | 9/1998 | Green |
| 5,810,718 A | 9/1998 | Akiba et al. |
| 5,817,013 A | 10/1998 | Ginn et al. |
| 5,820,546 A | 10/1998 | Ouchi |
| 5,836,867 A | 11/1998 | Speier et al. |
| 5,859,934 A | 1/1999 | Green |
| 5,863,256 A | 1/1999 | MacLean et al. |
| 5,876,325 A | 3/1999 | Mizuno et al. |
| 5,882,293 A | 3/1999 | Ouchi |
| 5,904,647 A | 5/1999 | Ouchi |
| 5,924,976 A | 7/1999 | Stelzer et al. |
| 5,931,833 A | 8/1999 | Silverstein |
| 5,976,146 A | 11/1999 | Ogawa et al. |
| 6,022,313 A | 2/2000 | Ginn et al. |
| 6,059,719 A | 5/2000 | Yamamoto et al. |
| 6,074,402 A | 6/2000 | Peifer et al. |
| 6,113,586 A | 9/2000 | Ouchi |
| 6,117,070 A | 9/2000 | Akiba |
| 6,132,368 A | 10/2000 | Cooper |
| 6,152,870 A | 11/2000 | Diener |
| 6,165,124 A | 12/2000 | Ouchi |
| 6,200,262 B1 | 3/2001 | Ouchi |
| 6,217,511 B1 | 4/2001 | Held |
| 6,223,100 B1 | 4/2001 | Green |
| 6,245,011 B1 | 6/2001 | Dudda et al. |
| 6,254,529 B1 | 7/2001 | Ouchi |
| 6,259,806 B1 | 7/2001 | Green |
| 6,261,284 B1 | 7/2001 | Ouchi |
| 6,293,908 B1 | 9/2001 | Fujikura et al. |
| 6,299,576 B1 | 10/2001 | Ouchi |
| 6,309,345 B1 | 10/2001 | Stelzer et al. |
| 6,309,397 B1 | 10/2001 | Julian et al. |
| 6,328,731 B1 | 12/2001 | Ouchi |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,968 B1 | 4/2002 | Kogasaka et al. |
| 6,394,998 B1 | 5/2002 | Wallace et al. |
| 6,398,726 B1 | 6/2002 | Ramans et al. |
| 6,458,074 B1 | 10/2002 | Matsui et al. |
| 6,459,926 B1 | 10/2002 | Nowlin et al. |
| 6,468,265 B1 | 10/2002 | Evans et al. |
| 6,491,701 B2 | 12/2002 | Tierney et al. |
| 6,493,608 B1 | 12/2002 | Niemeyer |
| 6,508,811 B2 | 1/2003 | Stihl |
| 6,514,197 B1 | 2/2003 | Ouchi et al. |
| 6,520,954 B2 * | 2/2003 | Ouchi .............................. 606/1 |
| 6,522,906 B1 | 2/2003 | Salisbury, Jr. et al. |
| 6,540,738 B2 | 4/2003 | Kurfess et al. |
| 6,565,578 B1 | 5/2003 | Peifer et al. |
| 6,574,355 B2 | 6/2003 | Green |
| 6,626,824 B2 | 9/2003 | Ruegg et al. |
| 6,659,939 B2 | 12/2003 | Moll et al. |
| 6,714,839 B2 | 3/2004 | Salisbury, Jr. et al. |
| 6,719,685 B2 | 4/2004 | Fujikura et al. |
| 6,720,988 B1 | 4/2004 | Gere et al. |
| 6,746,395 B2 | 6/2004 | Brommersma et al. |
| 6,764,439 B2 | 7/2004 | Schaaf et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,786,896 B1 | 9/2004 | Madhani et al. |
| 6,788,999 B2 | 9/2004 | Green |
| 6,799,065 B1 | 9/2004 | Niemeyer |
| 6,827,683 B2 | 12/2004 | Otawara |
| 6,832,984 B2 | 12/2004 | Stelzer et al. |
| 6,837,883 B2 | 1/2005 | Moll et al. |
| 6,850,817 B1 | 2/2005 | Green |
| 6,858,003 B2 | 2/2005 | Evans et al. |
| 6,860,848 B2 | 3/2005 | Wosnitza et al. |
| 6,866,671 B2 | 3/2005 | Tierney et al. |
| 6,869,395 B2 | 3/2005 | Page et al. |
| 6,890,294 B2 | 5/2005 | Niwa et al. |
| 6,893,393 B2 | 5/2005 | Carrillo |
| 6,893,441 B2 | 5/2005 | Brommersma et al. |
| 6,936,042 B2 | 8/2005 | Wallace et al. |
| 6,963,792 B1 | 11/2005 | Green |
| 6,997,931 B2 | 2/2006 | Sauer et al. |
| 6,999,852 B2 | 2/2006 | Green |
| 7,006,895 B2 | 2/2006 | Green |
| 7,025,720 B2 | 4/2006 | Boebel et al. |
| 7,033,347 B2 | 4/2006 | Appling |
| 7,060,024 B2 | 6/2006 | Long et al. |
| 7,060,025 B2 | 6/2006 | Long et al. |
| 7,063,661 B2 | 6/2006 | Okada |
| 7,169,167 B2 | 1/2007 | Chu |
| 7,204,804 B2 | 4/2007 | Zirps et al. |
| 7,220,227 B2 | 5/2007 | Sasaki et al. |
| 2002/0058857 A1 | 5/2002 | Smith |
| 2002/0183589 A1 | 12/2002 | Brommersma |
| 2003/0083545 A1 | 5/2003 | Smith |
| 2003/0176770 A1 | 9/2003 | Merril et al. |
| 2003/0216613 A1 | 11/2003 | Suzuki et al. |
| 2004/0006356 A1 | 1/2004 | Smith |
| 2004/0015050 A1 | 1/2004 | Goto et al. |
| 2004/0015051 A1 | 1/2004 | Sudakov et al. |
| 2004/0064015 A1 | 4/2004 | Goto et al. |
| 2004/0148035 A1 | 7/2004 | Barrett et al. |
| 2004/0158125 A1 | 8/2004 | Aznoian et al. |
| 2004/0162465 A1 | 8/2004 | Carrillo |
| 2004/0199049 A1 | 10/2004 | Parasher et al. |
| 2004/0210111 A1 | 10/2004 | Okada |
| 2004/0215058 A1 | 10/2004 | Zirps et al. |
| 2004/0230095 A1 | 11/2004 | Stefanchik et al. |
| 2004/0242959 A1 | 12/2004 | Nosel |
| 2004/0249411 A1 | 12/2004 | Suzuki |
| 2005/0027165 A1 | 2/2005 | Rovegno |
| 2005/0065399 A1 | 3/2005 | Sasaki et al. |
| 2005/0119522 A1 | 6/2005 | Okada |
| 2005/0119525 A1 | 6/2005 | Takemoto |
| 2005/0154255 A1 | 7/2005 | Jacobs |
| 2005/0182292 A1 | 8/2005 | Suzuki |
| 2005/0209505 A1 | 9/2005 | Okada |
| 2005/0222492 A1 | 10/2005 | Adams |
| 2005/0222494 A1 | 10/2005 | Prescott |
| 2005/0222495 A1 | 10/2005 | Okada et al. |
| 2005/0234297 A1 | 10/2005 | Devierre et al. |
| 2005/0267327 A1 | 12/2005 | Iizuka et al. |
| 2005/0267335 A1 | 12/2005 | Okada et al. |
| 2005/0288547 A1 | 12/2005 | Okada |
| 2006/0009677 A1 | 1/2006 | Lehmann et al. |
| 2006/0063975 A1 | 3/2006 | Hipp et al. |

| | | | |
|---|---|---|---|
| 2006/0069304 A1 | 3/2006 | Takemoto et al. | |
| 2006/0094927 A9 | 5/2006 | Okada | |
| 2006/0122459 A1 | 6/2006 | Aue | |
| 2006/0135846 A1 | 6/2006 | Hunt | |
| 2006/0149131 A1 | 7/2006 | Or | |
| 2006/0247495 A1 | 11/2006 | Bacher et al. | |
| 2006/0258902 A1 | 11/2006 | Spivey et al. | |
| 2006/0293560 A1 | 12/2006 | Nguyen et al. | |

FOREIGN PATENT DOCUMENTS

| | | |
|---|---|---|
| EP | 1502537 | 2/2005 |
| EP | 1 554 974 A1 | 7/2005 |
| JP | 5068667 | 3/1993 |
| JP | 6007288 | 1/1994 |
| JP | 6038921 A2 | 2/1994 |
| JP | 9103433 A2 | 4/1997 |
| WO | WO 9520341 | 8/1995 |
| WO | WO 9712557 | 4/1997 |
| WO | WO 2004021873 | 3/2004 |
| WO | WO 2004/035125 A1 | 4/2004 |

OTHER PUBLICATIONS

Partial International Search Report, PCT/US2007/011670.
International Search Report, PCT/US2007/011670, mailed Feb. 28, 2008.
Written Opinion for PCT/US2007/011670, mailed Feb. 28, 2008.

* cited by examiner

ENDOSCOPE TOOL COUPLING

BACKGROUND OF INVENTION

1. Field of Invention

The present invention relates to a coupling for mounting a surgical tool to an endoscope.

2. Discussion of Related Art

An endoscope is a medical instrument that can be inserted into the body cavity or organ of a patient for performing various surgical procedures. A working or biopsy channel typically extends along the entire length of the endoscope to allow passage of various instruments and/or tools into a patient. Optical instruments are conventionally provided in the endoscope for illuminating and remotely viewing the body cavity or organs.

An endoscope includes an elongated, flexible body within which extends the channels and instrumentation. A control handle is conventionally provided at the proximal end of the body for holding and manipulating the endoscope through the patient. One or more controls may be provided on the handle for operating various features of the endoscope. One or more ports are conventionally provided on the handle to provide access to the working or biopsy channel.

Surgical tools may be passed through the working or biopsy channel of the endoscope and into the patient for performing a desired surgical procedure. For example, a suturing device, such as disclosed in U.S. Patent Application Publication US 2005/0033319, may be passed through the working channel and into the patient to place one or more stitches in tissue. The tissue may be drawn together by tightening and securing the suture that has been placed in the tissue. Such a procedure may be beneficial for the treatment of various gastrointestinal or bariatric conditions, including treatments for GERD and obesity.

For some procedures, it may be desirable to precisely locate and maintain the distal end of the surgical tool at a particular position relative to either the distal end of the endoscope or a device located at the distal end of the endoscope.

SUMMARY OF INVENTION

In one illustrative embodiment of the invention, an endoscope tool coupling is provided for mounting a surgical tool to an endoscope. The endoscope tool coupling comprises a coupling body that is constructed and arranged to be mounted to a port of the endoscope, and a tool mount that is constructed and arranged to support the surgical tool on the coupling body. The tool mount is adjustably supported by the coupling body and lockable in a plurality of locked positions to maintain the surgical tool in each of a plurality of positions relative to the coupling body.

In another illustrative embodiment of the invention, an endoscope tool coupling is provided for mounting a surgical tool to an endoscope. The endoscope tool coupling comprises a coupling body that is constructed and arranged to be mounted to a port of the endoscope, and a tool mount that is constructed and arranged to support the surgical tool on the coupling body and to position a distal end of the surgical tool at a first position relative to a distal end of the endoscope. The tool mount cooperates with the coupling body to generate a preload for the surgical tool so as to maintain the distal end of the surgical tool at the first position.

In a further embodiment of the invention, an apparatus comprising an endoscope including an elongated endoscope body that is insertable into a body cavity or organ, and a tool coupling. The endoscope body has at least one working channel that extends from a proximal end to a distal end thereof. The working channel is adapted to allow passage of an elongated surgical tool therethrough. The tool coupling is constructed and arranged to mount a surgical tool at the proximal end of the endoscope body with the surgical tool extending through the working channel. The tool coupling is constructed and arranged to longitudinally adjust the distal end of the surgical tool to a plurality of positions relative to the distal end of the endoscope body and to maintain the distal end of the surgical tool at each of the plurality of positions.

In another illustrative embodiment of the invention, a method of mounting a surgical tool to an endoscope is provided. The method comprises acts of (a) mounting the surgical tool to a tool coupling provided at a working channel port located at a proximal end of the endoscope; and (b) adjusting the tool coupling to position a distal end of the surgical tool at a selected position relative to a distal end of the endoscope.

In a further illustrative embodiment of the invention, a method of mounting a surgical tool to an endoscope is provided. The method comprises acts of (a) mounting the surgical tool to a tool coupling provided at a working channel port located at a proximal end of the endoscope; (b) positioning a distal end of the surgical tool at a selected position relative to a distal end of the endoscope; and (c) preloading the surgical tool with the tool coupling to maintain the distal end of the surgical tool at the selected position.

BRIEF DESCRIPTION OF DRAWINGS

Various embodiments of the invention will now be described, by way of example, with reference to the accompanying drawings, in which.

DETAILED DESCRIPTION

Figure 1:
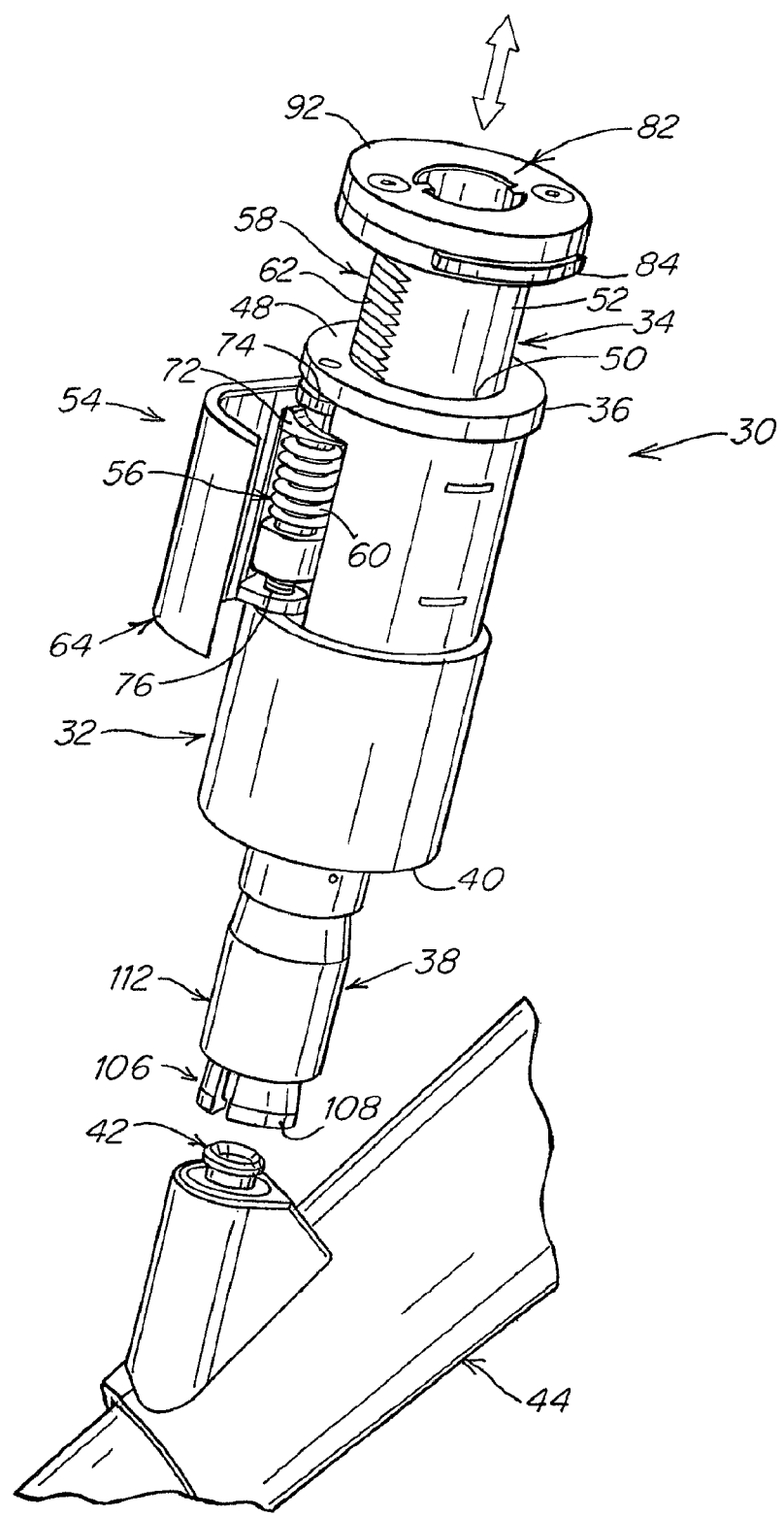
FIG. 1 is a perspective view of an endoscope tool coupling according to one illustrative embodiment shown in an unlocked configuration and detached from an endoscope.
Figure 2:
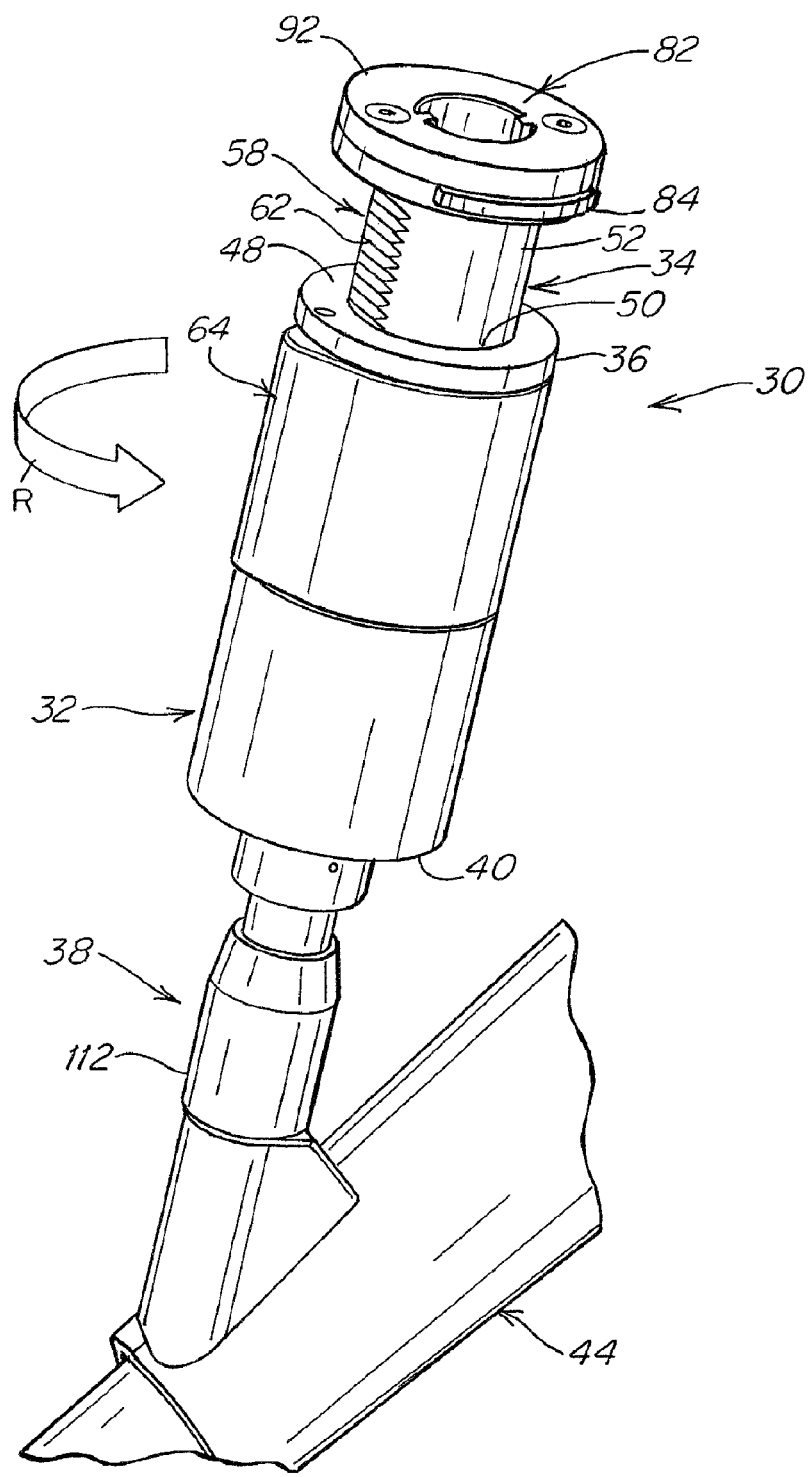
FIG. 2 is a perspective view of the endoscope tool coupling of FIG. 1 shown in a locked configuration and attached to the endoscope.

The present invention is directed to an endoscope tool coupling that facilitates the placement and positioning of a surgical tool within an endoscope. The tool coupling may be configured to accommodate differences in lengths between the surgical tool and the endoscope. In this manner, the tool coupling may allow a user to precisely position and maintain the distal end of a surgical tool in a desired location relative to the distal end of the endoscope despite differences and variations in lengths. The tool coupling may be configured to support and lock the surgical tool in place so that a user may remove his or her hands from the surgical tool without losing the desired position of the surgical tool relative to the endoscope.

The tool coupling may provide a hospital or medical personnel with the flexibility to readily use the same surgical tool with different length endoscopes, different length surgical tools with the same endoscope, or a combination of different length tools and different length endoscopes.

The tool coupling may have an adjustable configuration to accommodate variations in tool and/or endoscope lengths. In one embodiment, the tool coupling employs an arrangement that allows a user to easily increase or decrease the length of the coupling. The adjustability of the coupling length may be accomplished using a telescoping arrangement. However, it is to be appreciated that a telescoping arrangement is not required for each embodiment of the coupling.

A locking arrangement or mechanism may be provided to secure the coupling in a selected configuration for maintaining the surgical tool in a desired location relative to the endoscope. In one embodiment, an adjustment lock secures the coupling in a selected length that accommodates the particular lengths of the surgical tool and endoscope. However, it is to be appreciated that a locking arrangement for securing the coupling in a selected length is not required for each embodiment of the coupling.

The tool coupling may be configured to generate a preload on the surgical tool when the tool is positioned in a desired location relative to the endoscope. In one embodiment, the coupling may generate a preload by driving the surgical tool a predetermined distance in a distal direction. The preload may be applied once the configuration of the coupling has been established for the particular tool/endoscope arrangement. The tool coupling may employ a cam arrangement to generate the preload. However, it is to be appreciated that an arrangement for generating a preload is not required for each embodiment of the coupling.

The tool coupling may be configured to allow for the withdrawal and reintroduction of the same or a similar surgical tool without changing or impacting the original length adjustment and/or preload for the particular tool/endoscope arrangement. In one embodiment, the tool coupling includes an exchange port that is configured to receive and lock the surgical tool to the coupling independent of the length adjustment and/or preload application. However, it is to be appreciated that an exchange port is not required for each embodiment of the coupling.

In one embodiment, the tool coupling may be configured as a separate device that can be attached to various endoscopes. In another embodiment, the tool coupling may be an integrated component of the endoscope.

Although described in conjunction with an endoscope, it is to be appreciated that the tool coupling may be configured for use with other medical instruments that may benefit from a device that accommodates length variations between a particular medical instrument and a surgical tool that is to be used with the instrument and/or applies a preload to the tool.

For ease of understanding, and without limiting the scope of the invention, the tool coupling is described below as a stand-alone device that can be mounted to and detached from the working port of various endoscopes. It is to be understood, however, that any one or combination of the various features of the tool coupling described below may be incorporated into an endoscope as an integral component thereof.

In one illustrative embodiment shown in FIGS. 1-5, the tool coupling 30 includes a coupling body 32 and a tool mount 34 that is adjustably supported at a proximal end 36 of the coupling body 32. A connector 38 is provided at a distal end 40 of the coupling body 32 to mount the tool coupling to a port 42 of an endoscope 44. An internal passage 46 (FIG. 5) extends through the tool mount 34 and coupling body 32 to permit insertion of a surgical tool through the tool coupling 30 and into a working channel of the endoscope 44 via the port 42. The surgical tool may be supported on the proximal end of the tool mount.

In the illustrative embodiment, the tool mount 34 is slidably supported by the coupling body 32 in a telescoping arrangement so that the overall length of the tool coupling 30 may be selectively adjusted to accommodate variations in lengths between the surgical tool and the endoscope. As shown, the coupling body 32 has a generally cylindrical shape and includes a proximal end wall 48 with an opening 50 for receiving the tool mount 34. The tool mount 34 includes an elongated post 52 that is configured to be inserted into and slid through the end wall opening 50 and along the length of the coupling body 32 to adjust the length of the coupling.

The end wall opening 50 and the post 52 may be configured to have complementary shapes to help stabilize the coupling and prevent rotation of the post within the body. In one illustrative embodiment, the opening and post have complementary double D shapes with curved ends and flat sides. It is to be appreciated that the end wall opening 50 and the post 52 may employ other suitable configurations as would be apparent to one of skill.

An adjustment lock may be provided to secure the tool mount in any one of various positions relative to the coupling body. The adjustment lock may include at least one locking feature supported on the coupling body that is configured to engage with a corresponding locking feature provided on the tool mount.

Figure 3:
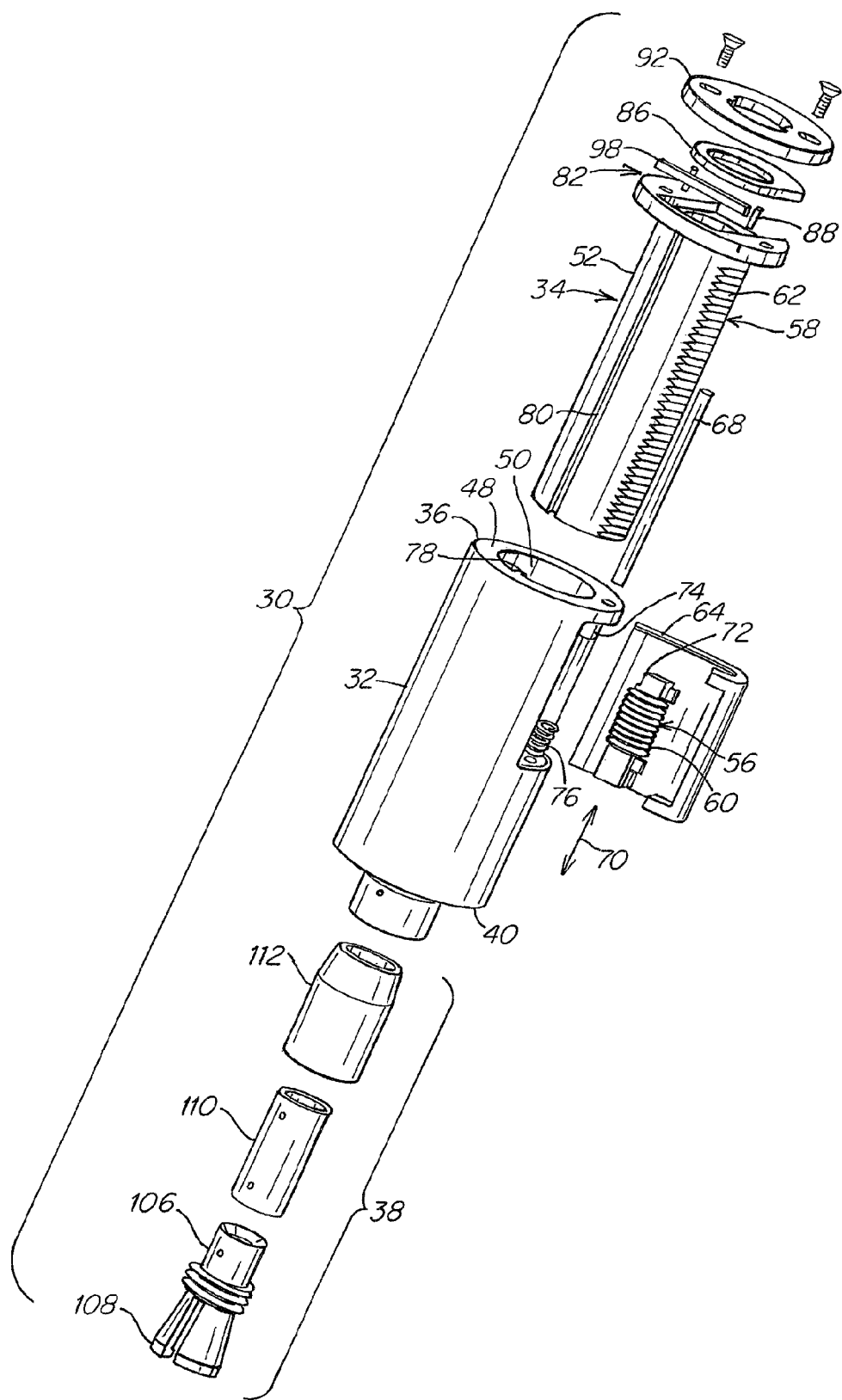
FIG. 3 is an exploded perspective view of the endoscope tool coupling of FIGS. 1-2.
Figure 4:
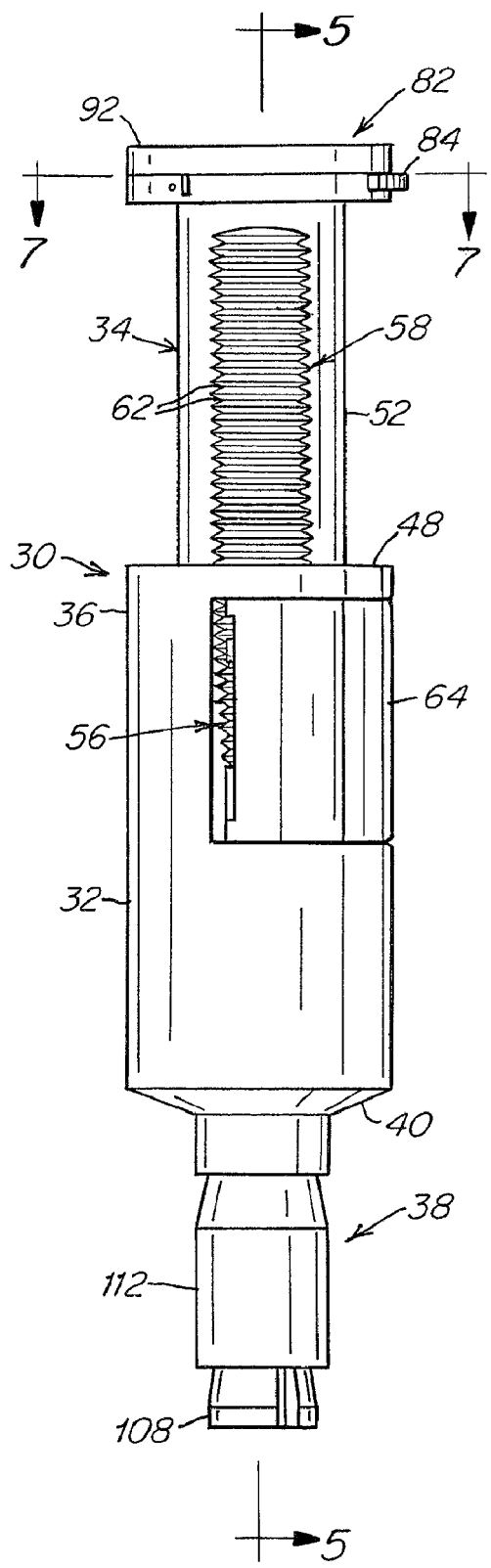
FIG. 4 is a side elevation view of the endoscope tool coupling of FIGS. 1-3.
Figure 5:
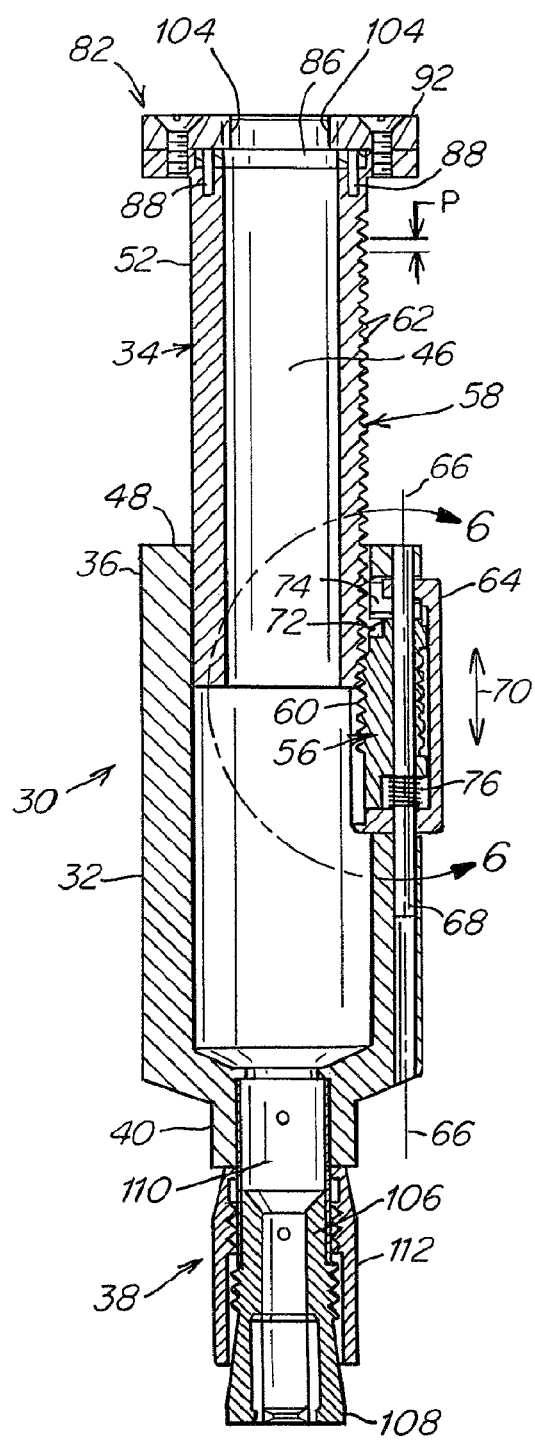
FIG. 5 is a cross-sectional view of the endoscope tool coupling taken along section line 5-5 of FIG. 4.

In one illustrative embodiment shown in FIGS. 1, 3, 5 and 6, the adjustment lock 54 includes an engagement member 56 that is movably supported on the coupling body 32 and a locking rack 58 that extends along the post 52 of the tool mount 34. The engagement member 56 includes a plurality of locking teeth 60 that engage corresponding locking teeth 62 provided on the locking rack 58. As shown in FIGS. 3 and 5, the locking rack 58 is longer than the engagement member 56 to provide axial adjustment therebetween. The tool mount 34 may be locked in a selected position by engaging the engagement member 56 with the locking rack 58 and released for adjustment by disengaging the engagement member from the rack.

The locking rack 58 may be configured to have a length for achieving a desired amount of total adjustment for the tool coupling. Additionally, the locking teeth 62 on the rack 58 may be spaced apart at a pitch P for achieving a desired amount of incremental adjustment. In one embodiment, the adjustment lock is configured to provide an overall length adjustment of approximately 2.0 inches with an incremental adjustment of approximately 0.075 inches. However, it is to be appreciated that the tool coupling may be configured to provide other suitable adjustments as would be apparent to one of skill in the art.

The adjustment lock 54 may include an actuator that can be operated to lock and unlock the tool mount. In one illustrative embodiment, the actuator includes a lever 64 that is pivotally supported by the coupling body 32 to actuate the engagement member 56 between a locked position and an unlocked position. With the lever 64 in a closed or locked position, as shown in FIGS. 2 and 4-6, the engagement member 56 engages a portion of the locking rack 58 and locks the tool mount 34 in a selected position. Actuating the lever 64 to an open or unlocked position, as shown in FIG. 1, disengages the engagement member 56 from the locking rack 58 to allow free axial or longitudinal movement of the tool mount 34 relative to the coupling body 32.

Figure 6:
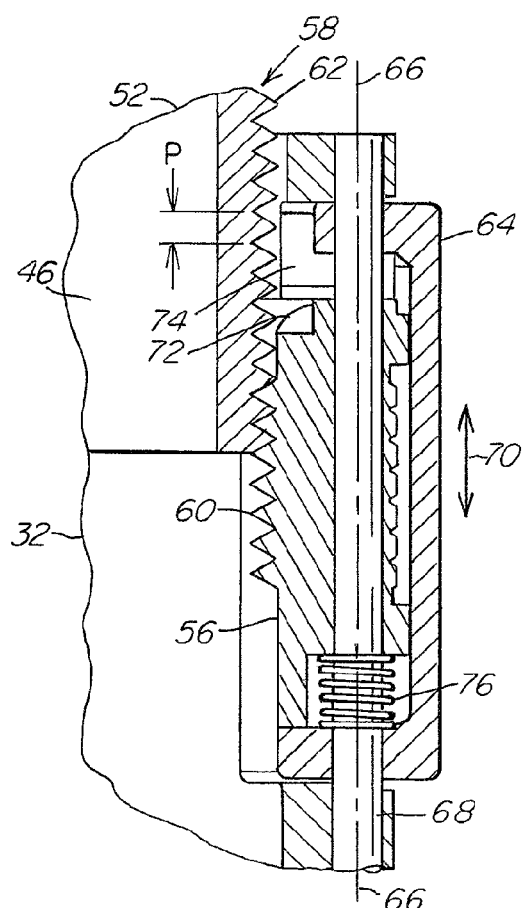
FIG. 6 is an enlarged view of the adjustment locking arrangement according to one illustrative embodiment taken along view line 6-6 of FIG. 5.

In one illustrative embodiment shown in FIGS. 3, 5 and 6, the engagement member 56 includes an engagement drum that is mounted to the lever 64 along the pivot axis 66 of the lever. In this manner, rotation R (FIG. 2) of the lever 64 about the pivot axis 66 causes the engagement drum 56 to also rotate about the pivot axis 66 into and out of engagement with the locking rack 58. The lever 64 and the engagement drum 56 are mounted to the coupling body 32 with an elongated pin 68.

In one embodiment, the locking teeth 60 of the engagement drum 56 have a circular shape extending about the pivot axis 66 and the locking teeth 62 along the locking rack 58 have a flat shape. This arrangement helps to facilitate and maintain engagement between the engagement drum 56 and the locking rack 58 as the drum is rotated by the lever 64. However, it is to be appreciated that the teeth for the engagement drum and the locking rack may employ other configurations apparent to one of skill in the art to engage and lock the tool mount.

As shown, the lever 64 may have a curved configuration that conforms to the shape of the coupling body 32 when the lever is placed in its closed, locked position. It is to be understood, however, that the lever may be configured to have other suitable shapes apparent to one of skill in the art.

In some situations, it may be desirable to preload the surgical tool in the distal direction when the tool is mounted to the endoscope with the tool coupling. A preload may help ensure that the surgical tool maintains a desired position at the distal end of the endoscope, particularly when the tool is employed with a flexible endoscope and the working channel for the tool is offset from the center axis of the scope. In this manner, the preload may accommodate differences between the arc lengths of the center axis of the endoscope and the working channel that could result from bending or flexing the endoscope. A preload may also provide resistance to or counteract the forces required to operate the surgical tool.

A desired preload may be generated by exerting a predetermined force on the surgical tool with the tool coupling. In one illustrative embodiment, the tool coupling may generate a preload on the surgical tool by driving the tool a predetermined distance in the distal direction relative to the coupling body when the position of the distal end of the tool has been selected and locked.

In one illustrative embodiment shown in FIGS. 3, 5 and 6, the engagement drum 56 is movable along the pin 68 in the axial direction so that axial movement 70 of the engagement drum 56, when it is engaged with the locking rack 58, causes the tool mount 34 to also move axially. In this manner, controlling the amount of axial movement 70 of the engagement drum 56 determines the amount of preload generated on the surgical tool.

In one illustrative embodiment, the engagement drum 56 includes a cam surface 72 at its proximal end that cooperates with a cam follower 74 on the coupling body 32. As the lever 64 is actuated to rotate R the engagement drum 56 into engagement with the locking rack 58, the engagement drum 56 is driven in the distal direction due to the interaction between the cam surface 72 and the cam follower 74. A spring 76 is provided at the distal end of the engagement drum 56 to bias the drum in the proximal direction so that the drum returns to its initial non-preload state when the lever actuates the engagement drum to the unlocked position (FIG. 1) for releasing the tool mount.

The cam arrangement may be configured to provide a predetermined amount of preload as the engagement drum is actuated to its locked position. In one embodiment, the cam arrangement is configured to drive the locked tool mount in the distal direction approximately 0.090 inches to generate a preload on the surgical tool. However, it is to be appreciated that the cam arrangement may be configured to provide other amounts of preload as would be apparent to one of skill in the art.

It may be desirable to provide a keying arrangement to ensure proper orientation between the tool mount and the coupling body. In one illustrative embodiment shown in FIG. 3, the coupling body 32 includes a key 78 at its proximal end that is configured to cooperate with a corresponding keyway 80 that extends along the length of the tool mount 34. Insertion of the tool mount 34 into the coupling body 32 requires alignment of the keyway 80 with the key 78. The keying arrangement may also be configured to provide a relatively close fit to minimize rotation between the tool mount and the coupling body.

The tool coupling may be configured to allow a user to detach a surgical tool and withdraw it from the endoscope while maintaining the selected length adjustment and/or preload. The same or similar tool may then be subsequently inserted through the tool coupling and positioned at the same location relative to distal end of the endoscope without having to readjust the coupling. For example, some surgical procedures may require the use of several of the same or different surgical devices to perform the procedure. This could involve the introduction and removal of various surgical tools through the same working channel of the endoscope. During such a procedure, it may be beneficial to repeatedly locate the distal working end of the surgical tools at a desired location relative to the distal end of the endoscope.

The tool coupling may include a tool exchange port that allows a user to readily exchange surgical tools without disrupting a previously set length adjustment and/or tool preload. In one illustrative embodiment as shown in FIGS. 1-5 and 8-9, the tool coupling includes a tool exchange port 82 at the proximal end of the tool mount 34. The tool exchange port 82 includes a tool lock 84 that is configured to engage with and lock one or more surgical tools to the tool mount. When the tool lock 84 is released, the surgical tool may be removed from the tool coupling and withdrawn from the endoscope.

In the illustrative embodiment, the tool lock 84 includes a locking clip 86 located adjacent the proximal end of the tool mount at the exchange port. The locking clip 86 is movable between a locked position (FIG. 8) to secure a tool to the tool mount and an unlocked position (FIG. 9) to release the tool from the tool mount. The locking clip 86 is configured to slide in a transverse direction across the internal passage 46 of the tool coupling between the locked and unlocked positions. The locking clip 86 may be retained by a pair of pins 88 that cooperate with elongated slots 90 in the clip and an end plate 92 that overlies the locking clip at the end of the tool mount.

Figure 8:
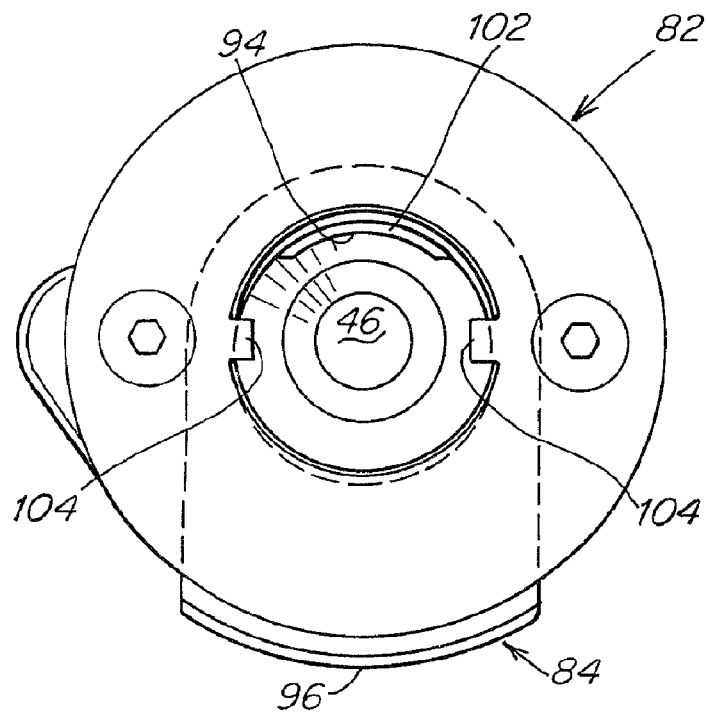
FIG. 8 is a proximal end view of the endoscope tool coupling of FIGS. 1-4 illustrating the exchange port tool lock in the locked position.
Figure 9:
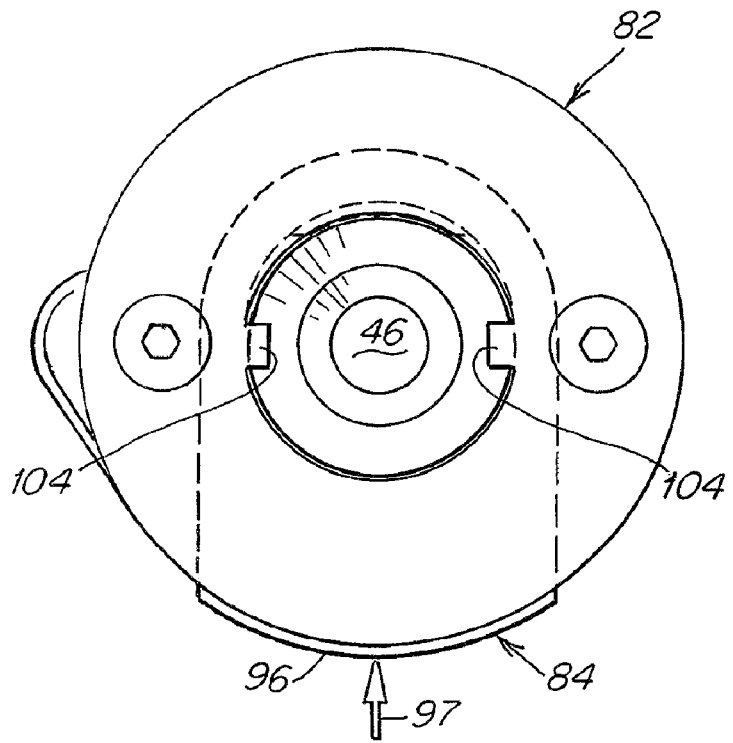
FIG. 9 is the proximal end view of FIG. 8 illustrating the exchange port tool lock in the unlocked position.

In the illustrative embodiment, the locking clip 86 includes at least one locking tooth 94 that is configured to mate with a corresponding recess (not shown) provided on the surgical tool. As shown in FIG. 8, the locking tooth 94 protrudes into the internal passage 46 of the exchange port in an inward radial direction when the locking clip is placed in the locked position.

The tool lock 84 may include an actuator that allows a user to move the locking clip to an unlocked position in which the locking tooth is disengaged from the tool. In one illustrative embodiment, the locking clip 86 includes an actuator button 96 that is located opposite to and extends away from the locking tooth 94. The actuator button 96 is configured to protrude from the side of the tool exchange port when the locking clip is in the locked position. To release the tool lock, the actuator button 96 is depressed 97 (FIG. 9) which causes the locking clip 86 to slide and disengage the locking tooth 94 from the tool so that the tool may be removed.

Figure 7:
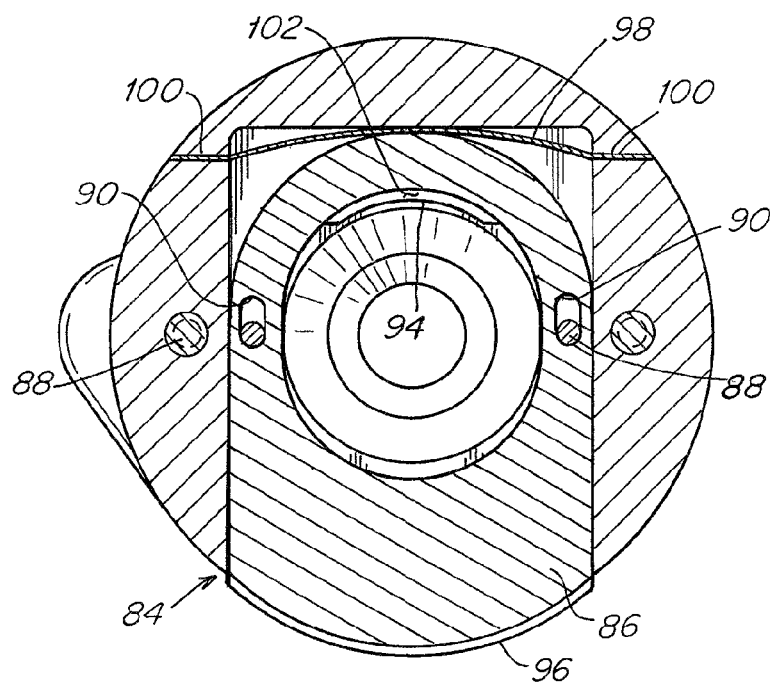
FIG. 7 is a cross-sectional view of the exchange port tool lock according to one illustrative embodiment taken along section line 7-7 of FIG. 4.

The locking clip may be biased to the locked position to ensure that the tool lock maintains a positive locking condition on the tool. In one illustrative embodiment shown in FIG. 7, the locking clip 86 is biased to the locked position using a spring 98 that is positioned against an end of the locking clip opposite the actuator button 96. In this manner, when the locking clip 86 is actuated to its unlocked position, by depressing the actuator button 96, the locking clip is driven against and deflects the spring 98 which generates a biasing force against the clip. When the actuator button 96 is released, the spring 98 urges the locking clip back to the locked position.

As shown in the illustrative embodiment, a flat spring 98 may be employed to bias the locking clip 86 to the locked position. As shown, each end of the spring 98 may be retained in a slot 100 that allows the ends of the spring to move as the spring moves between a deflected and non-deflected configuration. It is to be appreciated, however, that any suitable biasing arrangement apparent to one of skill in the art may be implemented with the exchange port.

To facilitate securing the surgical tool to the tool coupling, the tool lock may be configured to automatically move from the locked position toward the unlocked position as the surgical tool is introduced through the exchange port. In one illustrative embodiment, the locking tooth 94 is configured with a cam surface 102 that cooperates with the tool to drive the locking clip from its locked position. When the surgical tool is fully seated in the exchange port, the locking clip 86 engages the locking recess on the tool and locks the tool to the coupling.

A keying arrangement may be provided to ensure proper orientation and/or to prevent rotation of the surgical tool relative to the exchange port. In one illustrative embodiment shown in FIGS. 8-9, the tool exchange port 82 includes one or more keys 104 at its proximal end that are configured to cooperate with corresponding keyways or other suitable features provided on the surgical tool. Insertion of the tool into the exchange port 82 can only be accomplished when the keys 104 are aligned with the corresponding features on the tool resulting in the desired orientation and/or resistance to rotation between the tool and the port.

It is to be appreciated that the tool coupling may employ other suitable locking arrangements and locking features for securing a surgical tool to the exchange port as would be apparent to one of skill in the art.

As indicated above, the tool coupling may include a connector 38 at its distal end for mounting the coupling 30 to a port of the endoscope, when the coupling is not an integral component of the endoscope.

In one illustrative embodiment shown in FIGS. 1, 3 and 5, the connector 38 includes a connector body 106 that has a plurality of resilient fingers 108 that are configured to engage and securely lock onto a port 42 of the endoscope 44. The connector body 106 may be coupled to the distal end of the coupling body 32 with a connector coupler 110. A connector nut 112 is threaded on the connector body 106 to secure and release the connector by tightening or loosening the connector fingers 108 about the endoscope port mount. In this regard, the connector 38 employs a collet-like arrangement. It is to be understood, however, that other connector arrangements may be employed as would be apparent to one of skill in the art.

The various components of the tool coupling 30 may be fabricated from any suitable materials and employing any suitable manufacturing processes apparent to one of skill in the art. For example, the components may be fabricated from plastic materials, composite materials, metallic materials, and various combinations thereof. In one non-limiting embodiment, the coupling body 32, the tool mount 34, the tool mount end plate 92 and the connector body 106 may each be molded from a plastic material, such as polyetherimide. The engagement drum 56 may be molded from a plastic material, such as a TEFLON (fluoropolymer resin) filled acetal copolymer, and the lever 64 may be molded from a plastic material, such as an acetal copolymer. The locking clip 86 may be fabricated from a plastic material, such as DELRIN (acetal resin).

As indicated above, the tool coupling 30 may be employed to mount a surgical tool to an endoscope to facilitate the placement and positioning of a surgical tool within an endoscope. The tool coupling be used to accommodate differences in lengths between the surgical tool and the endoscope.

Figure 10:
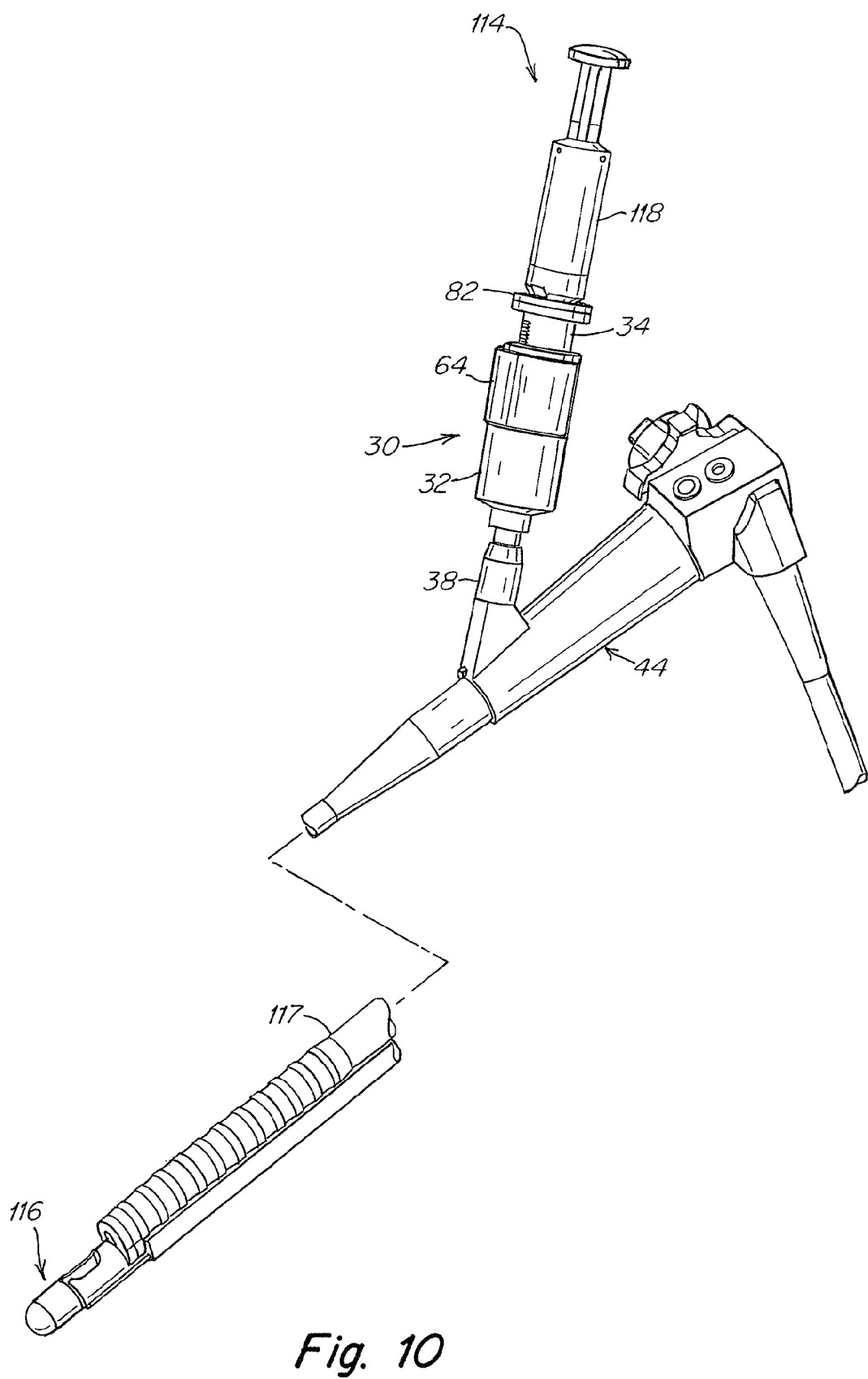
FIG. 10 is a perspective view of the endoscope tool coupling of FIGS. 1-9 attached to an endoscope and employed with an endoscopic suturing device according to one illustrative embodiment.

In one illustrative embodiment shown in FIG. 10, the tool coupling 30 is mounted to a working port of an endoscope 44. A surgical tool 114 is mounted to and extends through the tool coupling 30 and along the working channel of the endoscope 44. Positioning of the surgical tool 114 at a desired location relative to the distal end of the endoscope may be accomplished by adjusting the coupling 30 and then locking the coupling, as described above. If desired, the coupling 30 may be used to preload the tool within the endoscope, as described above.

In one illustrative embodiment, the surgical tool 114 is an endoscopic suturing device for endoscopically placing one or more stitches in tissue or muscle within a cavity or organ of a patient. For example, the suturing device may be particularly suited for treating various gastrointestinal or bariatric conditions, such as GERD and obesity. The suturing device may include a suturing capsule 116 that is mounted to the distal end of the endoscope body 117 and a control handle 118 that is mounted to the tool coupling 30 at the proximal end of the endoscope. The control handle 118 is coupled to a suturing mechanism that is positioned within the capsule 116. Operation of the suturing mechanism within a patient may be carried out through actuation of the control handle.

Proper operation of the suturing device 114 may require precisely locating and securing the suturing mechanism within the capsule. This may be accomplished by inserting the suturing mechanism through the tool coupling 30 and the working port and sliding the suturing mechanism along the length of the endoscope body 117. With the control handle 118 of the suturing device secured to the tool coupling 30, the coupling may be adjusted in the axial direction to precisely position the suturing mechanism within the capsule 116.

One embodiment of a suturing device particularly suited for endoscopic suturing is disclosed in U.S. Patent Application Publication US 2005/0033319, which is incorporated herein by reference. It is to be appreciated, however, that any suturing device or other surgical tools as would be apparent to one of skill in the art may be employed with the tool coupling.

When employed with a suturing device, it may be desirable to secure or retain a length of suture extending from the working channel of the endoscope. A suture retainer may allow a user to initially exert a desired amount of tension on the suture by hand and then maintain the suture at the desired tension hands free with the suture retainer. In this manner, the user can then control and manipulate the endoscope and the suturing device using both hands, if desired, without also having to maintain suture tension by hand.

Figure 20:
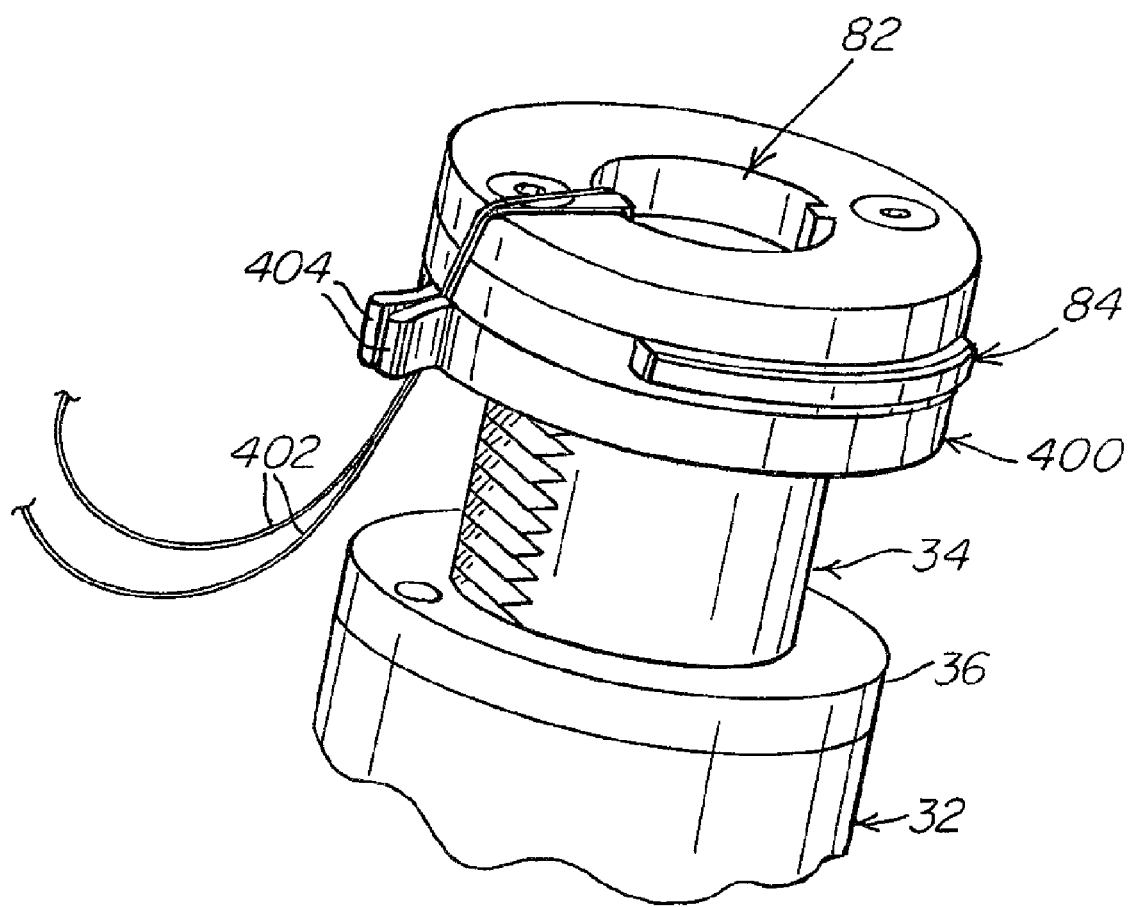
FIG. 20 is a partial perspective view of the endoscope tool coupling of FIG. 1 that includes a suture retainer according to another illustrative embodiment.

In one illustrative embodiment shown in FIG. 20, a suture retainer 400 may be provided on the tool mount 34 to secure one or more lengths of suture 402 to the tool coupling. As shown the suture retainer may be configured as a resilient clip that is attachable to the tool mount post. The clip includes a pair of tabs or lobes 404 that are urged together due to the resiliency of the clip. The suture may be pushed between the tabs 404 which retain the suture in place due to the opposing forces exerted by the tabs.

The suture retainer 400 may be formed of a plastic or metallic material that provides desired resiliency and/or retention properties. In one embodiment, the suture retainer includes a preformed steel clip that is overmolded with a soft polymer, such as PEBAX. If desired, the retainer may include only a steel clip. It is to be appreciated, however, that the suture retainer may be fabricated from other suitable material using any fabrication processes apparent to one of skill in the art. For example, the suture retainer may be molded from a plastic or elastomeric material. Alternatively, the suture retainer may be fabricated as an integral feature of the tool mount.

In some applications, the tool coupling may be used to mount a surgical tool that includes an integral tool mount for mating with the coupling body. In one illustrative embodiment shown in FIG. 11, the surgical tool 130 includes an integral tool mount 134 that is configured to be slidable within the coupling body 132. Similar to the embodiment described above, the tool mount 134 includes a locking rack 58 with a plurality of locking teeth 62 that may be engaged by the engagement drum of the coupling body 132 to lock the surgical tool 130 in any of a plurality of positions.

To remove the surgical tool from the endoscope, in contrast to the embodiment described above, it may be necessary to unlock and remove the tool mount 134, as part of the surgical tool, from the coupling body 132. To maintain the original adjustment set for the surgical tool, if it is to be remounted on the endoscope, it may be desirable to provide a stop or other feature that allows the tool mount to be easily repositioned at the same depth within the coupling body so as to relocate the distal end of the tool at its desired location. Such a feature would allow a user to repeatedly introduce the surgical tool through the endoscope without requiring readjustment of the tool coupling.

Figure 11:
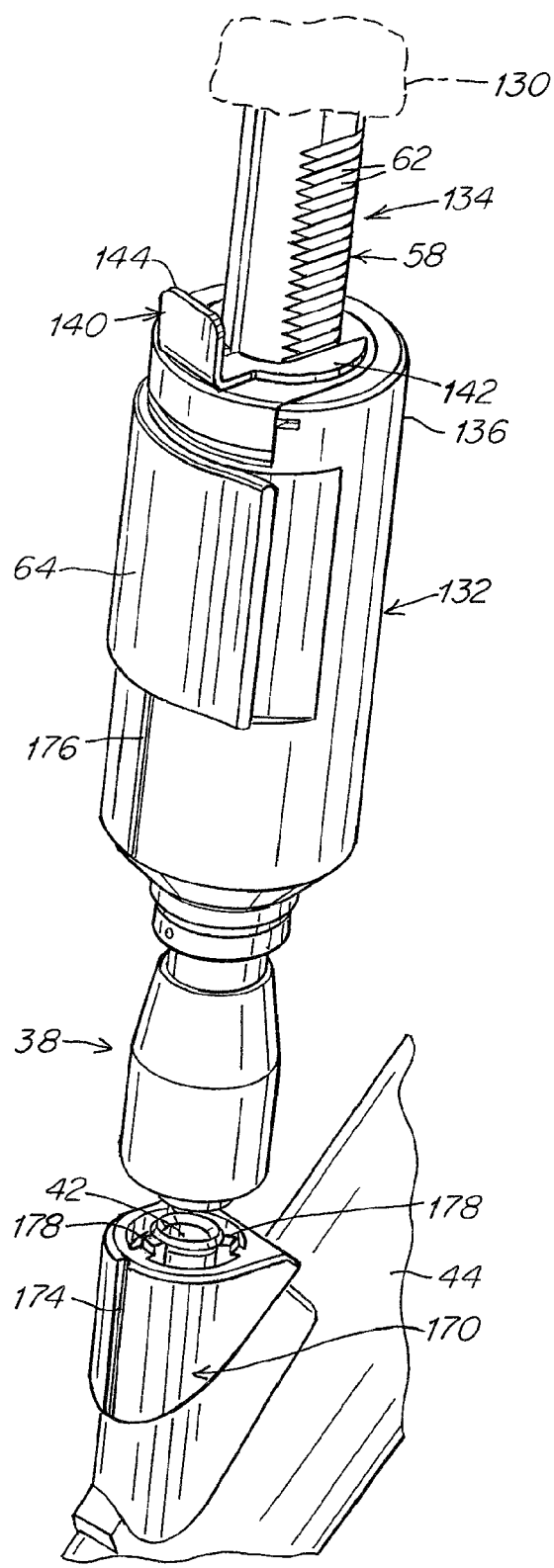
FIG. 11 is a perspective view of an endoscope tool coupling according to another illustrative embodiment shown in a locked configuration and detached from an endoscope.

In one illustrative embodiment shown in FIG. 11, the stop includes a clip 140 that is configured to be snapped onto the locking rack 58 of the tool mount 134 in close proximity to the proximal end 136 of the coupling body 132 after the surgical tool has been adjusted to its desired depth and locked to the coupling body. In this manner, should it be desirable to reintroduce the surgical tool into the coupling body after it has been removed, the tool can be slid into the coupling body until the clip 140 engages the end of the coupling body 132 which thereby places the tool in its desired position.

As illustrated, the clip 140 may include a C-shaped body 142 that is configured to mate with a tooth 62 on the tool mount 58 and engage the end of the coupling body 132. To facilitate handling of the clip, a handle 144 may be provided on the clip body 142. It is to be appreciated that other suitable stops, if desired, may be implemented with the tool coupling as would be apparent to one of skill in the art.

As described above, a preload may be generated by driving the tool mount 134 an additional distance in the distal direction after the desired length adjustment has been established for the particular tool and endoscope combination. To reduce the potential of binding the clip against the proximal end wall of the coupling body as the tool is being preloaded, which could interfere with proper operation of the tool coupling, the coupling body and/or the tool mount may be configured in a manner that accommodates the preload and reduces the effect of the clip being driven against the end wall of the coupling body.

Figure 12:
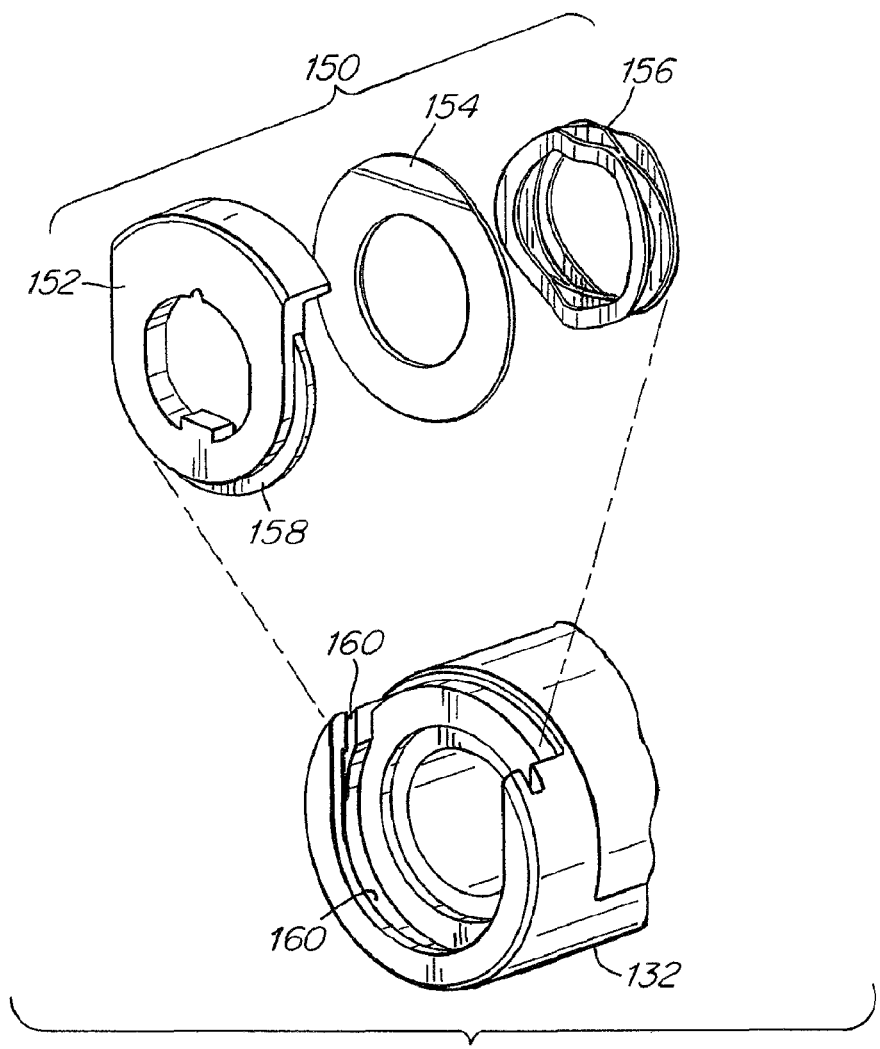
FIG. 12 is an exploded perspective view of the proximal end of the coupling body of FIG. 11 illustrating an embodiment of a resilient end plate for accommodating a preload configuration.

In one illustrative embodiment shown in FIG. 12, the coupling body 132 includes a resilient end wall 150 that is configured to allow the clip 140 to be placed against the end wall to reestablish the location of the distal end of the tool and allow the tool to be fully preloaded by driving the tool in the distal direction. The coupling body 132 includes an end plate 152 that is moveable in the axial direction, a spring plate 154 and a spring 156 that urges the spring plate 154 and the end plate 152 in the proximal direction. As shown, the end plate 152 may include a tongue or flange 158 that is configured to engage a corresponding slot or recess 160 provided in the coupling body 132 to mount and retain the resilient end wall 150 to the coupling body.

As the tool mount 134 is moved distally to preload the tool, the clip 140 similarly drives the end plate 152 in the distal direction against the biasing force of the spring 156. When the tool mount 134 is released from the coupling body 132, the end plate 152 returns to its initial proximal location due to the biasing force of the spring 156. It is to be understood that other suitable arrangements apparent to one of skill in the art may be employed to reduce potential binding between the clip and the coupling body.

In one embodiment, the spring 156 is configured as a wave spring formed of stainless steel flat wire. The spring has a spring rate of 90 lb/inch, a free length of 0.25 inches, a working height of 0.117 inches, and a load at working height of 12 lb. The end plate 152 may be fabricated from a plastic material, such as an acetyl copolymer, and the spring plate 154 may be fabricated from a metal, such as stainless steel. Of course, other suitable spring configurations and materials apparent to one of skill may be employed for the components of the spring plate mechanism.

In some instances, it may be desirable to maintain the surgical tool in a particular orientation on an endoscope. This may involve mounting the tool coupling to the endoscope in a particular orientation or alignment relative to the working port. This may also involve maintaining the tool coupling in the particular orientation once it has been mounted to the port.

Figure 13:
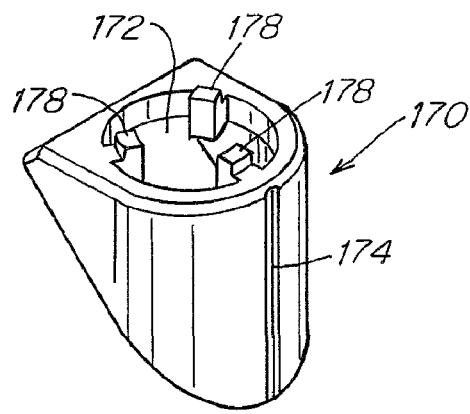
FIG. 13 is a perspective view of an alignment boss according to one illustrative embodiment.

In one illustrative embodiment shown in FIGS. 11 and 13, an alignment boss 170 may be provided for attachment to the working port of the endoscope. The boss 170 has a cap-like configuration that corresponds to the working port 42 so that the boss can be installed over and attached to the working port. The boss 170 has an opening 172 which provides access to the working port of the endoscope.

An alignment indicator may be provided on the boss 170 to provide a user with a visual reference for aligning the tool coupling with the port. As shown, the indicator may include an elongated recess or channel 174 which corresponds to a similar indicator 176 on the coupling body 132. The indicators 174, 176 may have a contrasting color relative to the boss 170 and the coupling body 132 so that it is easily identifiable by the user.

As indicated above, it may also be desirable to maintain the tool coupling in the aligned orientation once it has been mounted to the port. In one illustrative embodiment, the boss 170 includes one or more internal keys or fingers 178 that project into the boss opening 172. The keys 178 are arranged to fit between the fingers 108 of the connector 38 to prevent rotation of the connector on the port and maintain alignment of the tool coupling with the endoscope.

It is to be understood that an alignment boss is not a required component of the tool coupling. It is also to be appreciated that the alignment boss, if used, may utilize other suitable configurations and features apparent to one of skill in the art to facilitate alignment of the tool coupling with the endoscope and/or maintain a particular orientation between the tool coupling and the endoscope.

It is to be appreciated that the tool coupling may employ other arrangements for adjusting and locking the tool mount relative to the coupling body. Several such adjustment and locking arrangements are illustrated in FIGS. 14-19.

Figure 14:
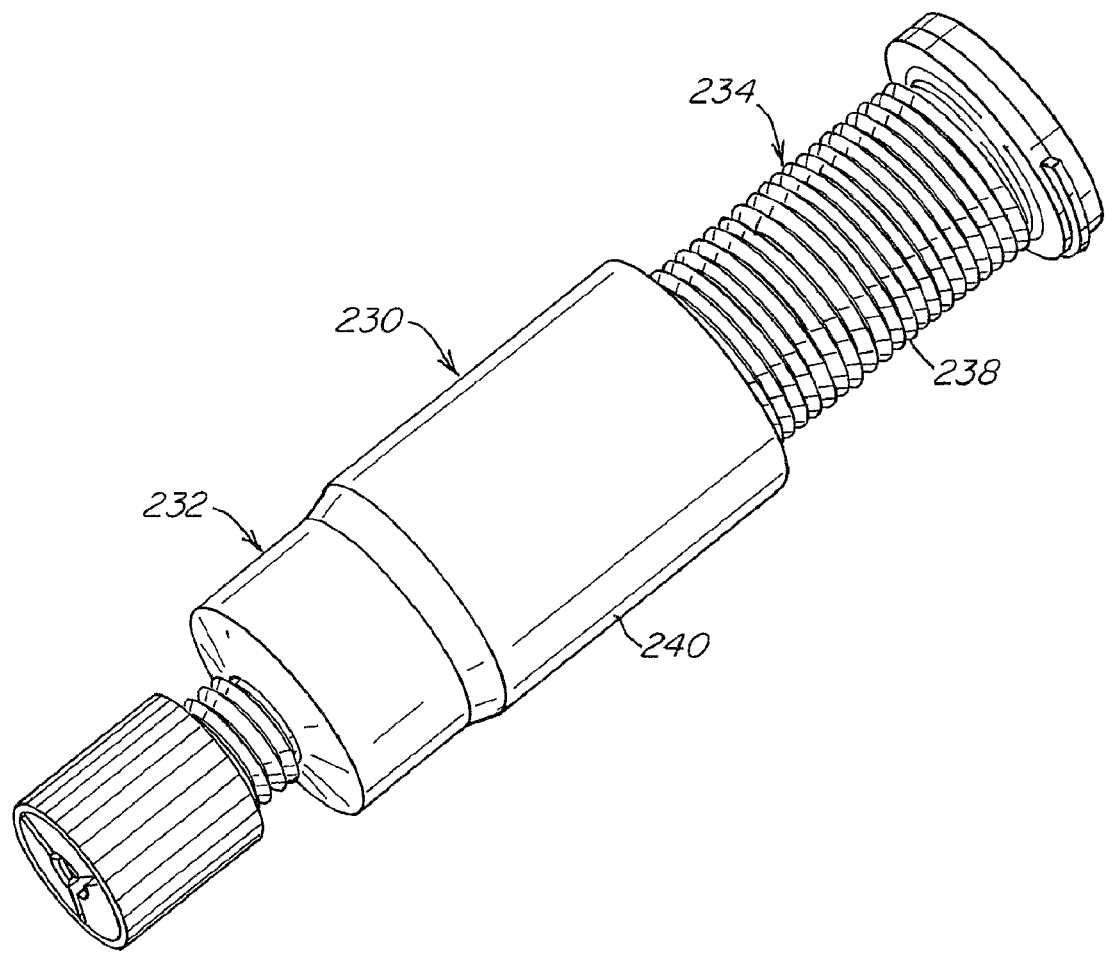
FIG. 14 is a perspective view of an endoscope tool coupling according to another illustrative embodiment.
Figure 15:
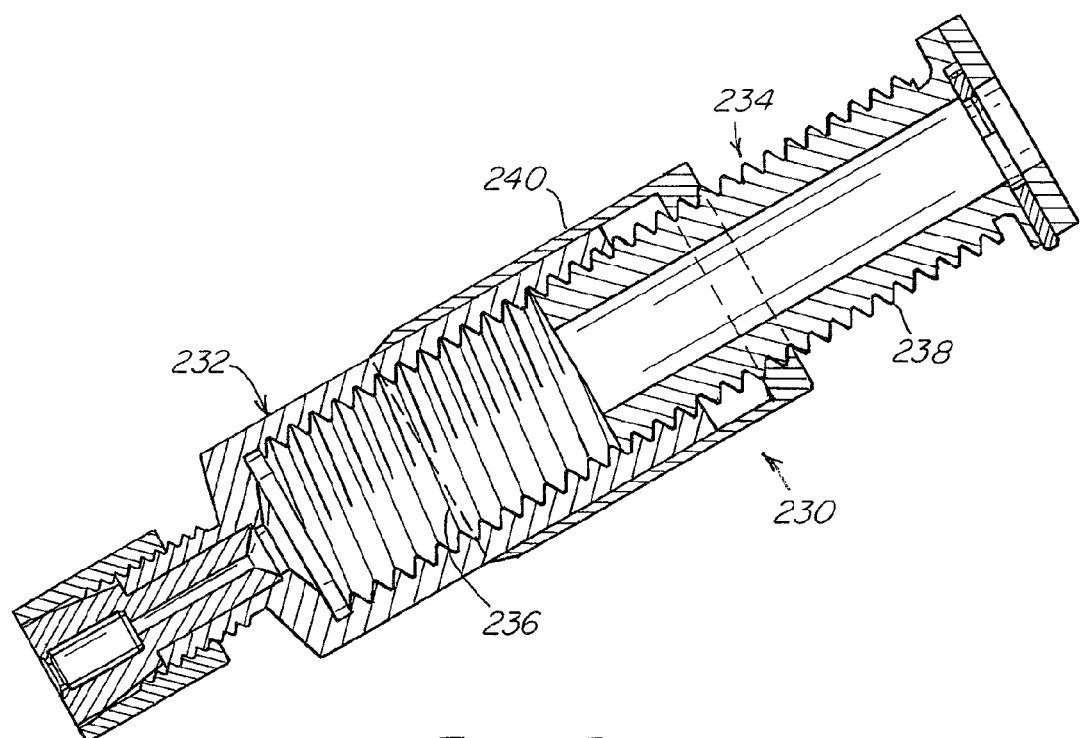
FIG. 15 is a cross-sectional view of the endoscope tool coupling of FIG. 14 shown in an unlocked configuration.
Figure 16:
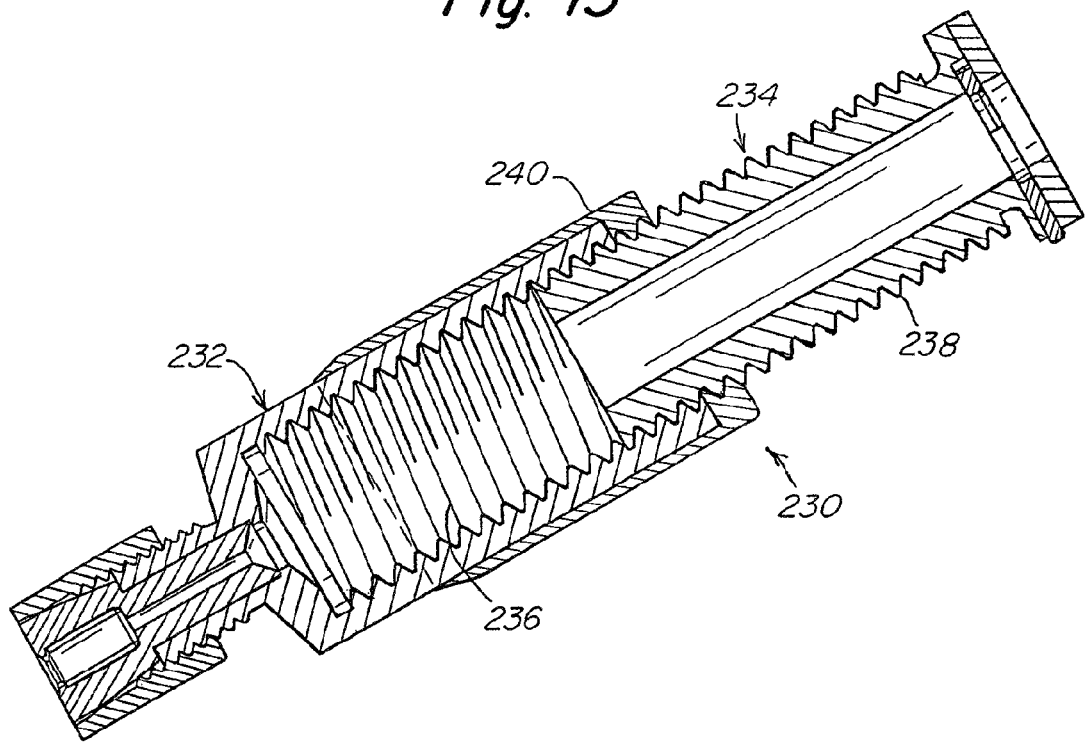
FIG. 16 is the cross-sectional view of FIG. 15 shown in a locked configuration.

In an illustrative embodiment shown in FIGS. 14-16, the tool coupling 230 may employ a threaded arrangement for adjusting the tool mount 234 relative to the coupling body 232. In this regard, adjustment of the tool mount 234 in the axial direction may be achieved by rotating the tool mount 234 relative to the coupling body 232. Once the desired adjustment has been achieved, the tool mount may be locked in place.

In the illustrative embodiment, the coupling body 232 includes an internal thread 236 along its length that cooperates with an external thread 238 along the length of the tool mount 234. Rotation of the tool mount 234 either clockwise or counterclockwise causes the tool mount to move axially in either the distal or proximal directions relative to the coupling body 232.

A locking nut 240 may be adjusted along the length of the tool mount 234 to lock and unlock the tool mount. As shown in FIG. 15, the tool mount 234 is unlocked by loosening the locking nut 240 so that it is spaced from the proximal end of the coupling body 232 which allows the tool mount 234 to be rotated relative to the coupling body. As shown in FIG. 16, the tool mount 234 is locked by tightening the locking nut 240 against the proximal end of the coupling body 232 which prevents rotation of the tool mount relative to the coupling body.

Figure 17:
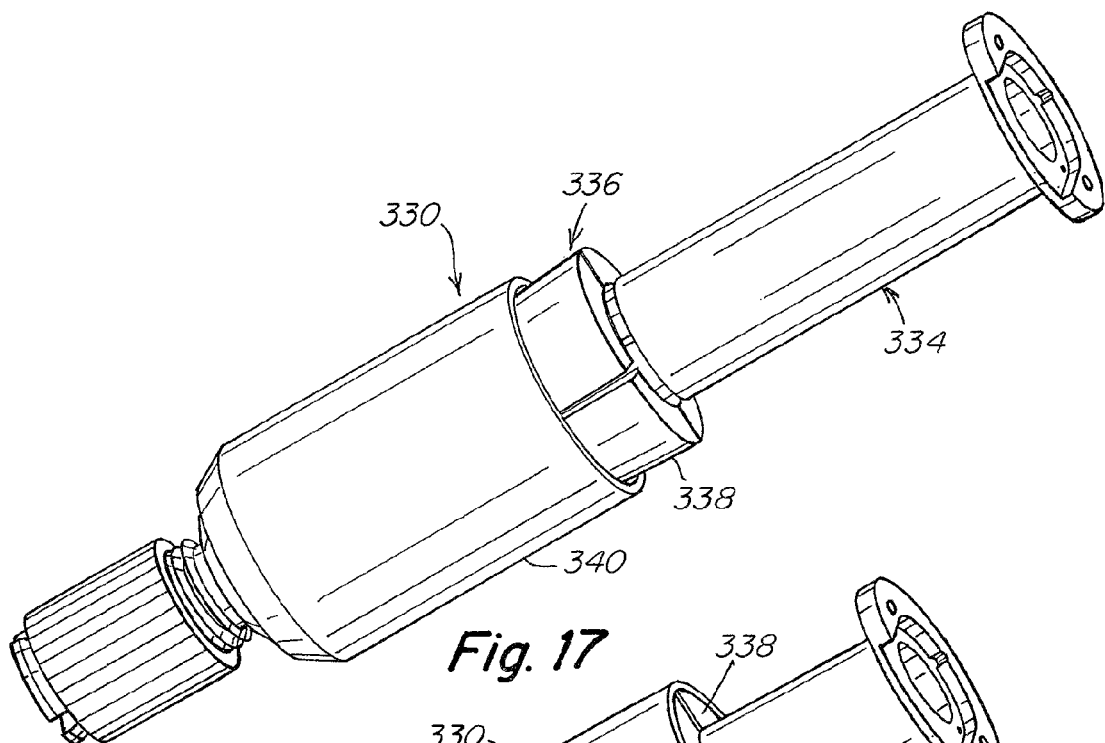
FIG. 17 is a perspective view of an endoscope tool coupling according to another illustrative embodiment shown in an unlocked configuration.
Figure 18:
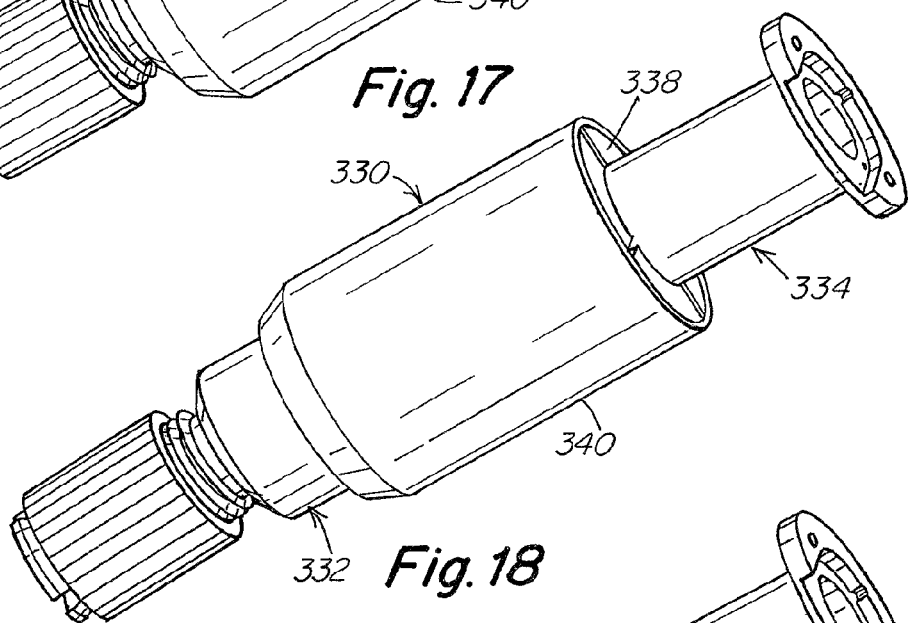
FIG. 18 is a perspective view of the endoscope tool coupling of FIG. 17 shown in a locked configuration.
Figure 19:
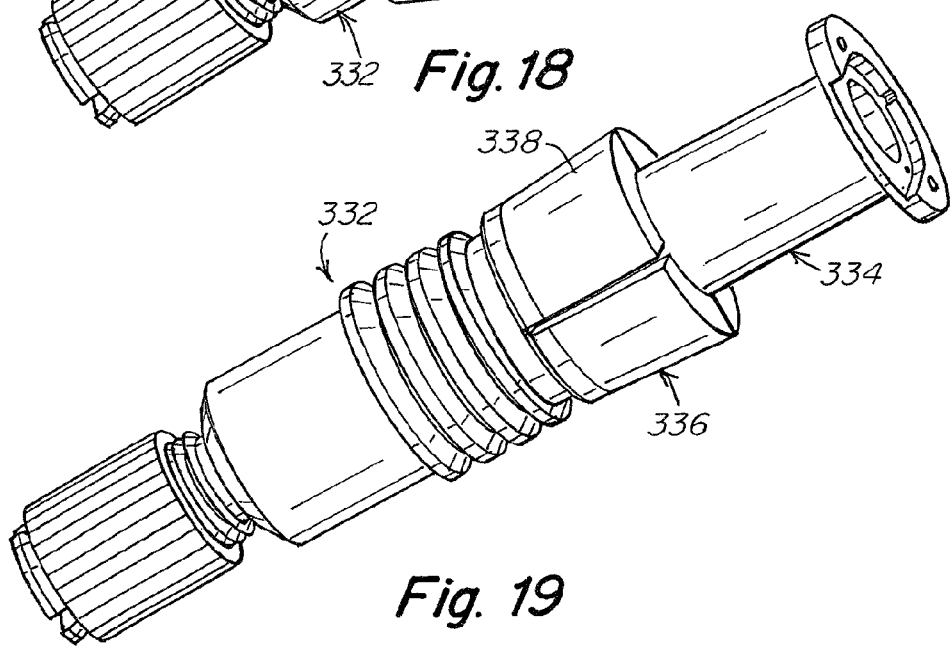
FIG. 19 is a perspective view of the endoscope tool coupling of FIGS. 17-18 shown with the locking nut removed.

In an illustrative embodiment as shown in FIGS. 17-19, the tool coupling 330 may employ a compression-type arrangement for adjusting the tool mount relative 334 to the coupling body 332. In this regard, the tool mount 334 may be slid in the axial direction relative to the coupling body 332 to achieve the desired length adjustment. Once the desired adjustment has been achieved, the tool mount 334 may be locked in place by applying a compressive force against the tool mount.

In the illustrative embodiment, the coupling body 332 includes a split-compression tube 336 through which the tool mount 334 may be slid axially in the distal and proximal directions to make desired length adjustments. The compression tube 336 includes a plurality of compression members 338 that may be flexed inwardly to engage and lock the tool mount.

A locking nut 340 is threaded on the coupling body 332 and may be adjusted in the proximal direction to lock the tool mount 334 and in the distal direction to release the tool mount. As shown in FIG. 17, the tool mount 334 is unlocked when the locking nut 340 is loosened toward the distal end of the coupling body 332 which allows the compression members 338 to expand in an outward radial direction away from the tool mount. As shown in FIG. 18, the tool mount 334 is locked by tightening the locking nut 340 toward the proximal end of the coupling body 332 and over the compression members 338 which compresses the tube 336 against the tool mount 334 with sufficient force to prevent movement of the tool mount relative to the coupling body.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An endoscope tool coupling for mounting a surgical tool to an endoscope, the endoscope tool coupling comprising:
   a coupling body that is constructed and arranged to be mounted to a port of the endoscope;
   a tool mount that is constructed and arranged to support the surgical tool on the coupling body, the tool mount adapted to be locked and unlocked relative to the coupling body, the tool mount being adjustably supported by the coupling body and lockable in a plurality of locked positions to maintain the surgical tool in each of a plurality of adjusted positions relative to the coupling body when locked, the tool mount being freely movable relative to the coupling body when unlocked to allow free adjustment of the tool mount, the tool mount being adjustable relative to the coupling body to adjust an overall length of the tool coupling, the tool mount being movable in an axial direction to adjust a distance between a proximal end of the coupling body and a proximal end of the tool mount; and
   an adjustment lock that is constructed and arranged to lock the tool mount to the coupling body in each of the plurality of adjusted positions, the adjustment lock including at least one locking feature that is constructed and arranged to engage the tool mount, the tool mount including a locking rack that is engageable by the at least one locking feature, the at least one locking feature including a plurality of first locking teeth and the locking rack including a plurality of second locking teeth that cooperate with the first locking teeth to lock the tool mount to the coupling body.

2. The endoscope tool coupling according to claim 1, wherein the tool mount is slidable in the axial direction.

3. The endoscope tool coupling according to claim 2, wherein the tool mount is supported in a telescoping configuration.

4. The endoscope tool coupling according to claim 3, wherein the tool mount includes an elongated post that is slidable within the coupling body.

5. The endoscope tool coupling according to claim 1, wherein the tool mount includes an elongated post that is slidable within the coupling body and the locking rack extends along a length of the post.

6. The endoscope tool coupling according to claim 1, wherein the adjustment lock includes an engagement drum that is rotatably supported by the coupling body between a locked position and an unlocked position, the engagement drum including the first locking teeth.

7. The endoscope tool coupling according to claim 6, wherein the first locking teeth have a circular configuration and the second locking teeth have a flat configuration.

8. The endoscope tool coupling according to claim 6, wherein the adjustment lock includes an actuator that is pivotally supported by the coupling body along a pivot axis to rotate the engagement drum between the locked position and the unlocked position.

9. The endoscope tool coupling according to claim 8, wherein the engagement drum is supported by the actuator along the pivot axis.

10. The endoscope tool coupling according to claim 6, wherein the engagement drum is movable in the axial direction to drive the tool mount in the axial direction as the engagement drum is rotated to the locked position to lock the tool mount in each of the plurality of locked positions.

11. The endoscope tool coupling according to claim 10, wherein the engagement drum includes a cam surface and the coupling body includes a cam follower that cooperates with the cam surface to drive the engagement drum in the axial direction as the engagement drum is rotated.

12. The endoscope tool coupling according to claim 1, wherein the tool mount includes a tool exchange port that is constructed and arranged to mount the surgical tool to the tool mount.

13. The endoscope tool coupling according to claim 12, wherein the tool mount includes a tool lock that is constructed and arranged to secure the surgical tool at the tool exchange port.

14. The endoscope tool coupling according to claim 13, wherein the tool lock includes a locking clip that is movable between a locked position to secure the surgical tool and an unlocked position to release the surgical tool.

15. The endoscope tool coupling according to claim 14, wherein the locking clip is slidably supported at the tool exchange port.

16. The endoscope tool coupling according to claim 15, wherein the locking clip is biased toward the locked position.

17. The endoscope tool coupling according to claim 1, further comprising a connector at a distal end of the coupling body to connect the coupling body to the port of the endoscope.

18. The endoscope tool coupling according to claim 1, further comprising a stop that is constructed and arranged to position the tool mount in an adjusted position.

19. The endoscope tool coupling according to claim 18, wherein the coupling body includes a resilient end wall that is constructed and arranged to be engaged by the stop in the adjusted position.

20. An endoscope tool coupling for mounting a surgical tool to an endoscope, the surgical tool having a length extending from a proximal end to a distal end thereof, the endoscope tool coupling comprising:
 a coupling body that is constructed and arranged to be mounted to a port at a proximal end of the endoscope;
 a tool mount that is constructed and arranged to support a proximal end portion of the surgical tool on the coupling body and to position the distal end of the surgical tool at a first position relative to a distal end of the endoscope, the tool mount adapted to cooperate with the coupling body to generate a preload by exerting a predetermined force in a direction along the length of the surgical tool so as to maintain the distal end of the surgical tool at the first position when the surgical tool is mounted to the endoscope, the tool mount being adjustably supported by the coupling body and lockable in a plurality of locked positions to maintain the surgical tool in each of a plurality of adjusted positions relative to the coupling body; and
 an adjustment lock that is constructed and arranged to lock the tool mount to the coupling body in each of the plurality of adjusted positions and to generate the preload, the adjustment lock including an engagement member that is movable in an axial direction to drive the tool mount in the axial direction to generate the preload for the surgical tool when the tool mount is locked in an adjusted position, the engagement member includes at least one locking feature that is constructed and arranged to engage the tool mount, the tool mount including a locking rack that is engageable by the at least one locking feature, the at least one locking feature including a plurality of first locking teeth and the locking rack including a plurality of second locking teeth that cooperate with the first locking teeth to lock the tool mount to the coupling body.

21. The endoscope tool coupling according to claim 20, wherein the tool mount includes an elongated post that is slidable within the coupling body and the locking rack extends along a length of the post.

22. The endoscope tool coupling according to claim 20, wherein the engagement member includes an engagement drum that is rotatably supported by the coupling body between a locked position and an unlocked position, the engagement drum including the first locking teeth.

23. The endoscope tool coupling according to claim 22, wherein the first locking teeth have a circular configuration and the second locking teeth have a flat configuration.

24. The endoscope tool coupling according to claim 22, wherein the adjustment lock includes an actuator that is pivotally supported by the coupling body along a pivot axis to rotate the engagement drum between the locked position and the unlocked position.

25. The endoscope tool coupling according to claim 24 wherein the engagement drum is supported by the actuator along the pivot axis.

26. The endoscope tool coupling according to claim 25, wherein the engagement drum is movable in the axial direction to drive the tool mount in the axial direction as the engagement drum is rotated to the locked position to generate the preload for the surgical tool.

27. The endoscope tool coupling according to claim 26, wherein the engagement drum includes a cam surface and the coupling body includes a cam follower that cooperates with the cam surface to drive the engagement drum in the axial direction as the engagement drum is rotated.

28. The endoscope tool coupling according to claim 20, wherein the tool mount includes a tool exchange port that is constructed and arranged to mount the surgical tool to the tool mount.

29. The endoscope tool coupling according to claim 28, wherein the tool mount includes a tool lock that is constructed and arranged to secure the surgical tool at the tool exchange port.

30. The endoscope tool coupling according to claim 20, further comprising a connector at a distal end of the coupling body to connect the coupling body to the port of the endoscope.

31. The endoscope tool coupling according to claim 20, further comprising a stop that is constructed and arranged to position the tool mount in an adjusted position.

32. The endoscope tool coupling according to claim 31, wherein the coupling body includes a resilient end wall that is constructed and arranged to be engaged by the stop in the adjusted position.

33. The endoscope tool coupling according to claim 20, wherein the tool mount is adapted to be driven a predetermined distance in a distal direction relative to the coupling body when the tool mount is locked in a locked position to generate the preload.

34. An endoscope tool coupling for mounting a surgical tool to an endoscope, the endoscope tool coupling comprising:
a coupling body that is adapted to be mounted to a port of the endoscope;
a tool mount that is adapted to support the surgical tool on the coupling body, the tool mount being adjustably supported by the coupling body and lockable in a plurality of locked positions to maintain the surgical tool in each of a plurality of adjusted positions relative to the coupling body; and
an adjustment lock that is adapted to lock the tool mount to the coupling body in each of the plurality of adjusted positions, the adjustment lock adapted to engage the tool mount in a locked position to lock the tool mount to the coupling body and to disengage from the tool mount in an unlocked position to unlock the tool mount from the coupling body and allow adjustment of the tool mount relative to the coupling body, the adjustment lock including at least one locking feature that is adapted to engage the tool mount in the locked position, the tool mount including a locking rack that is to be engaged by the at least one locking feature in the locked position, the at least one locking feature including a plurality of first locking teeth and the locking rack including a plurality of second locking teeth that cooperate with the first locking teeth in the locked position to lock the tool mount to the coupling body, the plurality of first and second locking teeth being disengaged in the unlocked position to unlock the tool mount.

35. The endoscope tool coupling according to claim 34, wherein the tool mount is adjustable relative to the coupling body to adjust an overall length of the tool coupling.

36. The endoscope tool coupling according to claim 35, wherein the tool mount is movable in an axial direction to adjust a distance between a proximal end of the coupling body and a proximal end of the tool mount.

37. The endoscope tool coupling according to claim 36, wherein the tool mount is slidable in the axial direction.

38. The endoscope tool coupling according to claim 37, wherein the tool mount is supported in a telescoping configuration.

39. The endoscope tool coupling according to claim 38, wherein the tool mount includes an elongated post that is slidable within the coupling body.

40. The endoscope tool coupling according to claim 34, wherein the tool mount includes an elongated post that is slidable within the coupling body and the locking rack extends along a length of the post.

41. The endoscope tool coupling according to claim 34, wherein the adjustment lock includes an engagement drum that is rotatably supported by the coupling body between the locked position and the unlocked position, the engagement drum including the first locking teeth.

42. The endoscope tool coupling according to claim 41, wherein the first locking teeth have a circular configuration and the second locking teeth have a flat configuration.

43. The endoscope tool coupling according to claim 41, wherein the adjustment lock includes an actuator that is pivotally supported by the coupling body along a pivot axis to rotate the engagement drum between the locked position and the unlocked position.

44. The endoscope tool coupling according to claim 43, wherein the engagement drum is supported by the actuator along the pivot axis.

45. The endoscope tool coupling according to claim 41, wherein the engagement drum is movable in the axial direction to drive the tool mount in the axial direction as the engagement drum is rotated to the locked position to lock the tool mount in each of the plurality of locked positions.

46. The endoscope tool coupling according to claim 45, wherein the engagement drum includes a cam surface and the coupling body includes a cam follower that cooperates with the cam surface to drive the engagement drum in the axial direction as the engagement drum is rotated to the locked position.

47. The endoscope tool coupling according to claim 34, wherein the tool mount includes a tool exchange port that is constructed and arranged to mount the surgical tool to the tool mount.

48. The endoscope tool coupling according to claim 47, wherein the tool mount includes a tool lock that is adapted to secure the surgical tool at the tool exchange port.

49. The endoscope tool coupling according to claim 48, wherein the tool lock includes a locking clip that is movable between a locked position to secure the surgical tool and an unlocked position to release the surgical tool.

50. The endoscope tool coupling according to claim 49, wherein the locking clip is slidably supported at the tool exchange port.

51. The endoscope tool coupling according to claim 50, wherein the locking clip is biased toward the locked position.

52. The endoscope tool coupling according to claim 34, further comprising a connector at a distal end of the coupling body that is adapted to connect the coupling body to the port of the endoscope.

* * * * *